(12) United States Patent
Tanner et al.

(10) Patent No.: US 6,248,118 B1
(45) Date of Patent: Jun. 19, 2001

(54) HEAT ACTIVATED SURGICAL FASTENER

(75) Inventors: Howard M. Tanner, Logan, UT (US);
Hugh H. Trout, III, Bethesda, MD (US)

(73) Assignee: EVA Corporation, Bethesda, MD (US)

( * ) Notice: Subject to any disclaimer, the term of this patent is extended or adjusted under 35 U.S.C. 154(b) by 0 days.

(21) Appl. No.: 09/442,768

(22) Filed: Nov. 18, 1999

Related U.S. Application Data

(63) Continuation-in-part of application No. 09/213,233, filed on Dec. 17, 1998, now Pat. No. 5,997,556, which is a continuation-in-part of application No. 08/958,524, filed on Oct. 27, 1997, now Pat. No. 5,957,940, which is a continuation-in-part of application No. 08/896,415, filed on Jul. 18, 1997, now Pat. No. 5,944,750.
(60) Provisional application No. 60/051,209, filed on Jun. 30, 1997.

(51) Int. Cl.[7] .................................................. A61B 17/08
(52) U.S. Cl. ............................................................. 606/153
(58) Field of Search ................................... 606/151, 153, 606/155, 113, 138, 194, 195, 198, 213–216, 232; 623/1, 11, 12

(56) References Cited

U.S. PATENT DOCUMENTS 5,904,697 * 5/1999 Gifford, III et al. ................. 606/155

* cited by examiner

*Primary Examiner*—Olik Chaudhuri
*Assistant Examiner*—Hoa B. Trinh
(74) *Attorney, Agent, or Firm*—John N. Coulby; Collier Shannon Scott, PLLC

(57) ABSTRACT

The present invention is directed to an electrically activated thermally inserted fastener assembly for use in a surgical procedure for securing a first component to a second component. The fastener assembly in accordance with the present invention comprises a securing assembly for securing the first component to the second component, and insertion assembly for inserting the securing assembly through the first component and at least a portion of the second component. A heat transmitting portion of the fastener assembly burns an incision in the first and second component to permit insertion of the fastener.

14 Claims, 36 Drawing Sheets

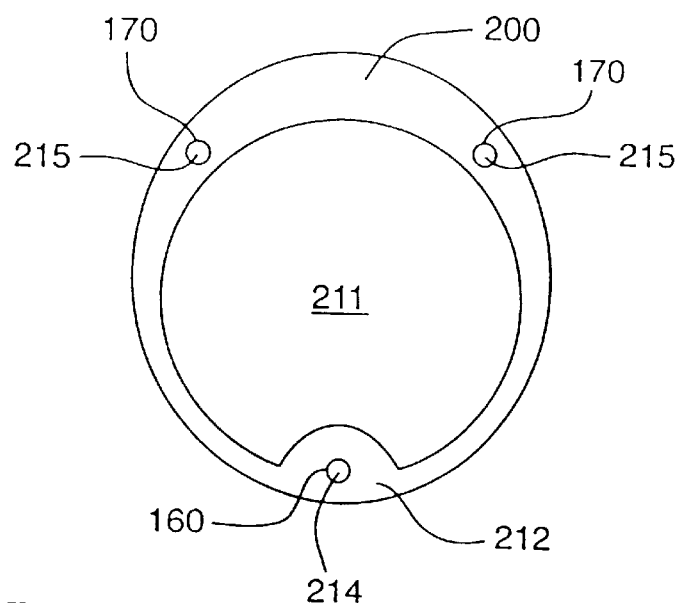
FIG. 14
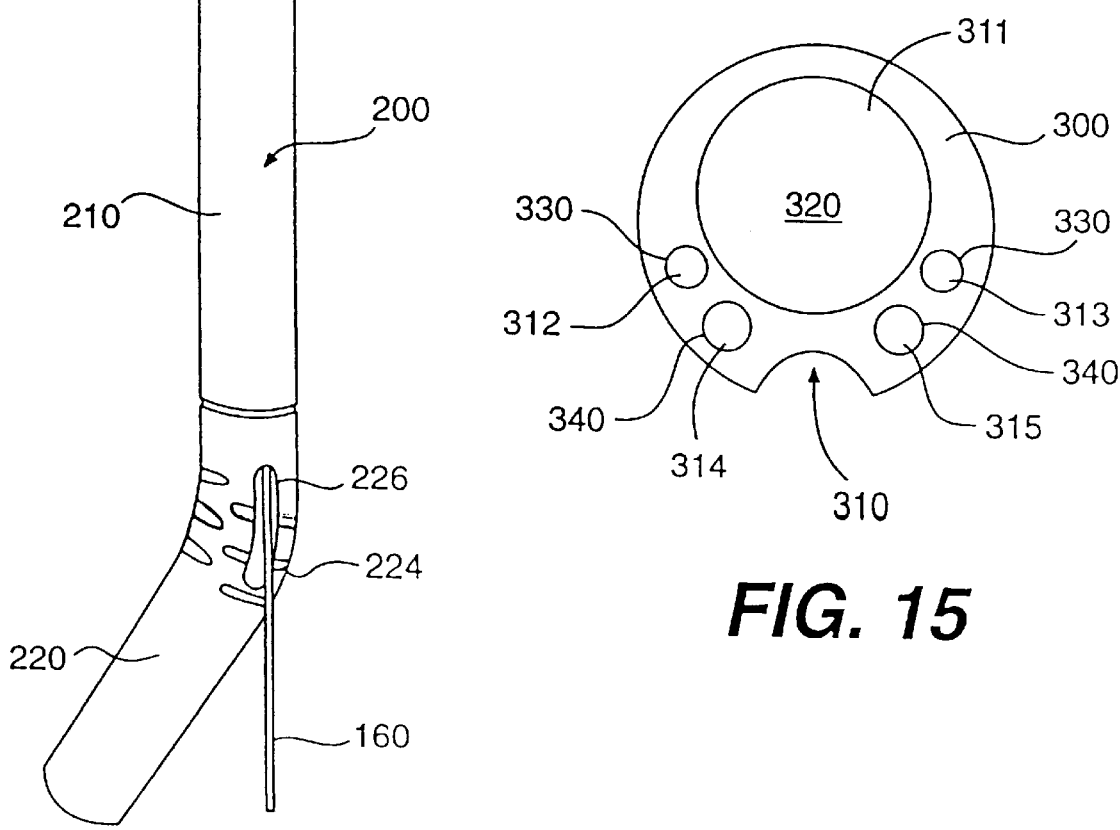
FIG. 15
FIG. 16

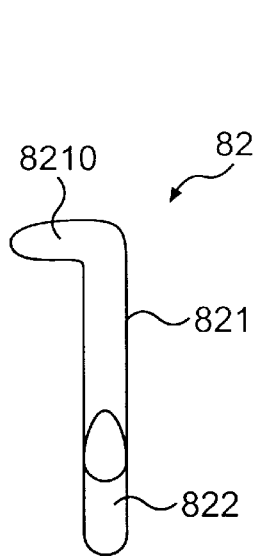
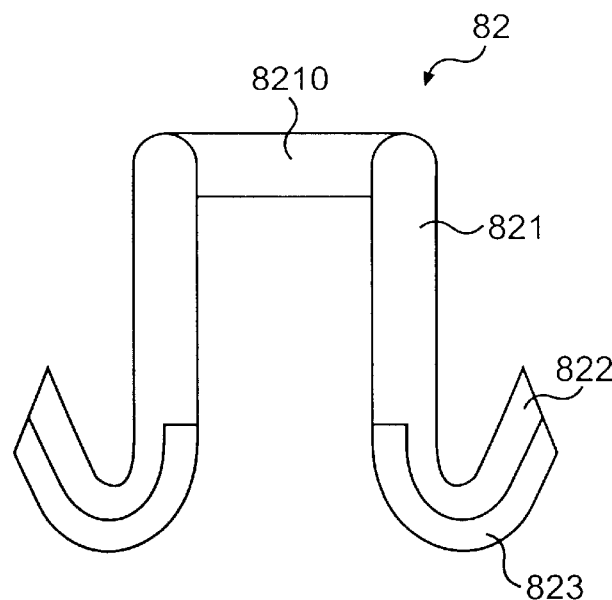
FIG. 68
FIG. 69
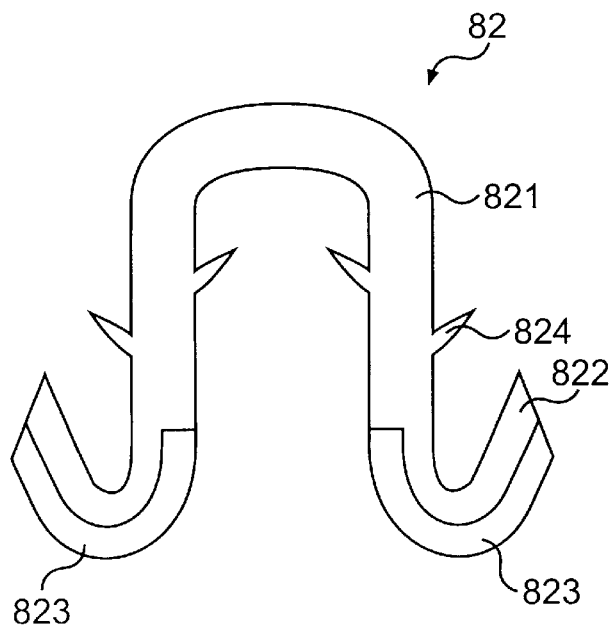
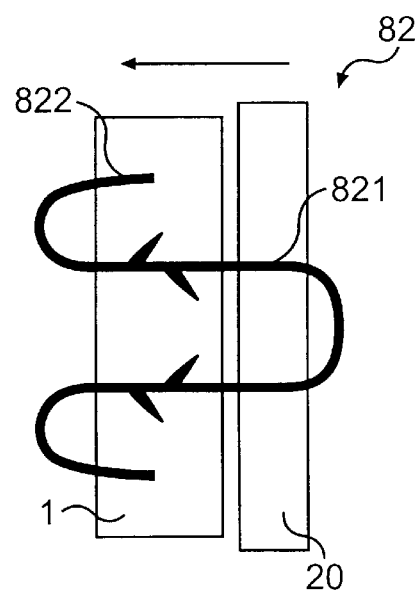
FIG. 70
FIG. 71

HEAT ACTIVATED SURGICAL FASTENER

CROSS REFERENCE TO RELATED APPLICATIONS

This application is a continuation-in-part of U.S. patent application Ser. No. 09/213,233, filed Dec. 19, 1998, now U.S. Pat. No. 5,997,556, which is a continuation-in-part of U.S. patent application Ser. No. 08/958,524, filed Oct. 27, 1997, now U.S. Pat. No. 5,957,940, which is a continuation-in-part of U.S. patent application Ser. No. 08/896,415, filed Jul. 18, 1997, now U.S. Pat. No. 5,944,750, which claims priority to U.S. Provisional Patent Application No. 60/051,209, filed Jun. 30, 1997.

BACKGROUND OF THE INVENTION

1. Field of the Invention

The present invention relates to a surgical fastener. In particular, the present invention is directed to a thermal fastener for use in surgical procedures to secure a first component to a second component such that the fastener extends through the first component and at least a portion of the second component.

2. Description of Related Art

An aneurysm is a ballooning of the wall of an artery resulting from the weakening of the artery due to disease or other conditions. Left untreated, the aneurysm will frequently rupture, resulting in loss of blood through the rupture and death.

Aortic aneurysms are the most common form of arterial aneurysm and are life threatening. The aorta is the main artery which supplies blood to the circulatory system. The aorta arises from the left ventricle of the heart, passes upward and bends over behind the heart, and passes down through the thorax and abdomen. Among other arterial vessels branching off the aorta along its path, the abdominal aorta supplies two side vessels to the kidneys, the renal arteries. Below the level of the renal arteries, the abdominal aorta continues to about the level of the fourth lumbar vertebrae (or the navel), where it divides into the iliac arteries. The iliac arteries, in turn, supply blood to the lower extremities and perineal region.

It is common for an aortic aneurysm to occur in that portion of the abdominal aorta between the renal arteries and the iliac arteries. This portion of the abdominal aorta is particularly susceptible to weakening, resulting in an aortic aneurysm. Such an aneurysm is often located near the iliac arteries. An aortic aneurysm larger than about 5 cm in diameter in this section of the aorta is ominous. Left untreated, the aneurysm may rupture, resulting in rapid, and usually fatal, hemorrhaging. Typically, a surgical procedure is not performed on aneurysms smaller than 5 cm because no statistical benefit exists in performing such procedures.

Aneurysms in the abdominal aorta are associated with a particularly high mortality rate; accordingly, current medical standards call for urgent operative repair. Abdominal surgery, however, results in substantial stress to the body. Although the mortality rate for an aortic aneurysm is extremely high, there is also considerable mortality and morbidity associated with open surgical intervention to repair an aortic aneurysm. This intervention involves penetrating the abdominal wall to the location of the aneurysm to reinforce or replace the diseased section of the aortic aneurysm. A prosthetic device, typically a synthetic tube graft, is used for this purpose. The graft serves to exclude the aneurysm from the circulatory system, thus relieving pressure and stress on the weakened section of the aorta at the aneurysm.

Repair of an aortic aneurysm by surgical means is a major operative procedure. Substantial morbidity accompanies the procedure, resulting in a protracted recovery period. Further, the procedure entails a substantial risk of mortality. While surgical intervention may be indicated and the surgery carries attendant risk, certain patients may not be able to tolerate the stress of intra-abdominal surgery. It is, therefore, desirable to reduce the mortality and morbidity associated with intra-abdominal surgical intervention.

In recent years, methods have been developed to attempt to treat an aortic aneurysm without the attendant risks of intra-abdominal surgical intervention. Among them are inventions disclosed and claimed in Kornberg, U.S. Pat. No. 4,562,596 for Aortic Graft, Device and Method for Performing an Intraluminal Abdominal Aortic Aneurysm Repair; Lazarus, U.S. Pat. No. 4,787,899 for Intraluminal Graft Device, System and Method; and Taheri, U.S. Pat. No. 5,042,707 for Intravascular Stapler, and Method of Operating Same.

Kornberg discloses an aortic graft comprising a flexible tubular material having a plurality of struts to lend the graft stability and resiliency. The struts have angled hooks with barbs at their upper ends which are securely attached to the inside of the aorta above the aneurysm. Kornberg's graft is inserted using a tubular device also disclosed in his patent. Kornberg, however, only anchors the proximal end of the graft. Kornberg claims that the downward flow of blood holds the distal graft securely in place, so that no mechanical attachment is necessary distally. The blood pressure in the abdominal aorta, however, is typically in the magnitude of 130 mm of mercury (Hg). In spite of the direction of flow of blood through the graft, proximal to distal, substantial back pressure within the aneurysm will result unless the distal end is also mechanically attached to the aorta in a manner that prevents substantial leakage of blood between the graft and the aorta. Without distal attachment, the device of Kornberg will not effectively exclude the weakened arterial wall at the site of the aneurysm from the forces and stress associated with the blood pressure.

Lazarus discloses a grafting system that employs a plurality of staples mounted in the proximal end of the graft. Lazarus's staples are forced through the aorta wall by means of a balloon catheter. As does Kornberg, Lazarus discloses staples mounted only in the proximal end of the graft. There is no teaching or suggestion in Lazarus, U.S. Pat. No. 4,787,899 as to the desirability of, let alone means for, mechanically attaching the graft to the distal aorta below the level of the aneurysm.

Taheri discloses an articulatable stapler for implanting a graft in a blood vessel. The stapler is in the form of an elongated catheter with a plurality of segments mounted on the distal end of the catheter. The segments have beveled faces and are connected to each other by hinges. A stylet runs through the catheter to the most distal segment. The most distal segment is moved, in conjunction with the other segments, into a firing position that is substantially perpendicular to the main catheter body by the action of pulling on the stylet. The staple is implanted by using two other stylets which act as fingers to bend the staple into its attachment position.

Taheri, however, appears to be a single-fire design which can only implant one staple at a time. After each stapler is implanted, Taheri's design apparently requires that the catheter be removed before another staple is loaded. In addition, Taheri's does not teach or suggest an appropriate density of staples to secure a graft against the pulsatile blood flow of the aorta. Pressures within the aorta range from 120 mm Hg pressure to 200 mm Hg pressure. Without adequate attachment, the graft may leak around the edges continuing to allow life threatening pressures to develop in the aneurysm, and may not even remain in place.

Hence, although in recent years certain techniques have been developed that may reduce the stress, morbidity, and risk of mortality associated with surgical intervention to repair aortic aneurysms, none of the systems that have been developed effectively treat the aneurysm and exclude the affected section of aorta from the pressures and stresses associated with circulation. None of the devices disclosed in the references provide a reliable and quick means to reinforce an aneurysmal artery. In addition, all of the prior references require a sufficiently large section of healthy aorta surrounding the aneurysm to ensure attachment of the graft. The neck of the aorta at the cephalad end (i.e., above the aneurysm) is usually sufficient to maintain a graft's attachment means. However, when an aneurysm is located near the iliac arteries, there may be an ill-defined neck or no neck below the aneurysm. Such an ill-defined neck would have an insufficient amount of healthy aortic tissue to which to successfully mount a graft. Furthermore, much of the abdominal aorta wall may be calcified which may make it extremely difficult to attach the graft to the wall.

There are a number of shortcomings with the presently available graft products and their fixation within the abdominal aorta. Although sizing of "tube" or "bifurcated" grafts is radiographically assessed prior to surgery, it is necessary for the surgeon to have a large selection of graft lengths and diameters on hand to ensure an appropriate surgical outcome. Additional shortcomings include the placement of a "circular" profile graft with an associated fixation device within an essentially "ovoid" profile vessel and the use of attachment means which fasten only to the insubstantial, structurally compromised (diseased) intima and media levels of the vessel wall. Research has exposed yet another problem which indicates that the necks of the post-surgical aorta increase in size for approximately twelve months, regardless of whether the aneurysm experiences dimensional change. This phenomenon can result in perigraft leaks and graft migration.

OBJECTS OF THE INVENTION

It is an object of the present invention to provide a fastener that can be thermally positioned to secure a surgical component to a vessel.

It is an object of the present invention to firmly fasten a graft to the adventitia of the vessel wall to prevent migration of the graft.

It is another object of the present invention to provide fastener assemblies that replace sutures.

It is another object of the present invention to provide a fastener assembly that secures a first component to a second component.

It is another object of the present invention to provide a fastener assembly having means to prevent its removal once in an inserted position.

It is another object of the present invention to provide a fastener assembly having means for promoting tissue ingrowth.

It is another object of the present invention to provide a fastener assembly that uses the generation of heat to enable its insertion.

It is another object of the present invention to provide a fastener assembly having a heat transmitting portion.

It is another object of the present invention to provide a fastener assembly having a heat transmitting portion that creates an incision in a first component and a portion of a second component.

SUMMARY OF THE INVENTION

The present invention is directed to a fastener assembly for use in a surgical procedure for securing a first component to a second component. The fastener assembly in accordance with the present invention comprises securing means for securing the first component to the second component, and insertion means for inserting the securing means through the first component and at least a portion of the second component.

In accordance with the present invention, the insertion means may comprise incision creating means for creating an incision in the first component and at least a portion of the second component. The incision creating means applies heat to create the incision. The incision creating means creates the incision by burning the first component and at least a portion of the second component only in the area of the incision to prevent damage to the components.

In accordance with the present invention, the securing means comprises means for preventing removal of the fastener assembly from the first and second component. The means for preventing removal may include at least one projection on the fastener assembly extending from the securing means. The means for preventing removal may include at least one aperture in the securing means. The at least one aperture promotes tissue ingrowth. The at least one aperture may include a self-expanding material located therein, wherein the self-expanding material expands upon insertion of the fastener assembly within the first component and the second component. The self-expanding material promotes tissue ingrowth.

The present invention is also directed to a method of securing a first component to a second component. The method comprises the steps of providing a fastener assembly, positioning the fastener assembly adjacent the first component at a desired location, applying energy to the fastener assembly to selectively heat a portion of the fastener assembly such that a portion of the first component and at least a portion of the second component are heated to create an incision, and applying a force to the fastener assembly to insert the fastener assembly through the portion of the first component and at least a portion of the second component.

BRIEF DESCRIPTION OF THE DRAWINGS

The invention will now be described in conjunction with the following drawings in which like reference numerals designate like elements and wherein:

FIG. 14 is an end view of the IntraVascular Angiography (IVA) based repair system according to the embodiment of FIG. 13;

FIG. 15 is an end view of the visualization device depicted in FIG. 13;

FIG. 16 is another perspective view of the IntraVascular Angiography (IVA) based repair system illustrating the guide wire and articulation cables exiting the housing of the repair system;

FIG. 68 is a schematic view of a variation of the fastener of FIG. 66;

FIG. 69 is a front schematic view of the fastener of FIG. 68;

FIG. 70 is a schematic view of a fastener according to another embodiment of the present invention;

FIG. 71 is a schematic view of the fastener of FIG. 70 in an inserted position.

DETAILED DESCRIPTION OF PREFERRED EMBODIMENTS

The following descriptions of the preferred embodiments of the present invention are described, for purpose of example, in connection with the repair of an abdominal aortic aneurysm. The inventors of the present subject matter contemplate that the embodiments described herein are capable of use in the repair of other vessels and in other procedures. Thus, it is intended that the present invention cover the modifications and variations of the invention, provided they come within the scope of the appended claims and their equivalents.

Repair Graft

Reference will now be made in detail to embodiments of grafts according to the present invention for repair of abdominal aortic aneurysms, an example of which is illustrated in FIGS. 1–11.

Figure 1:
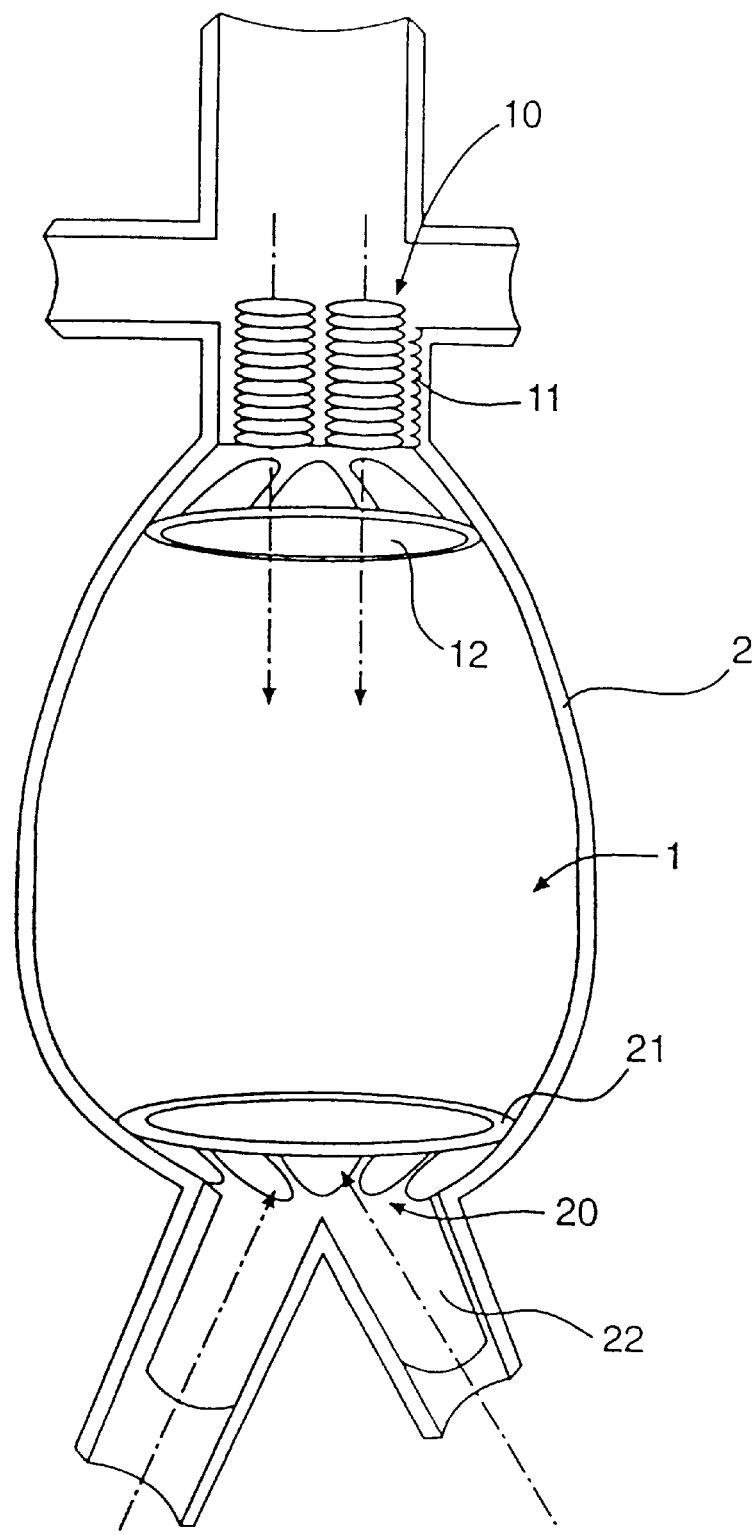
FIG. 1 is a perspective view of a prosthetic bifurcated tube graft and bifurcated cuff according to an embodiment of the present invention.
Figure 3:
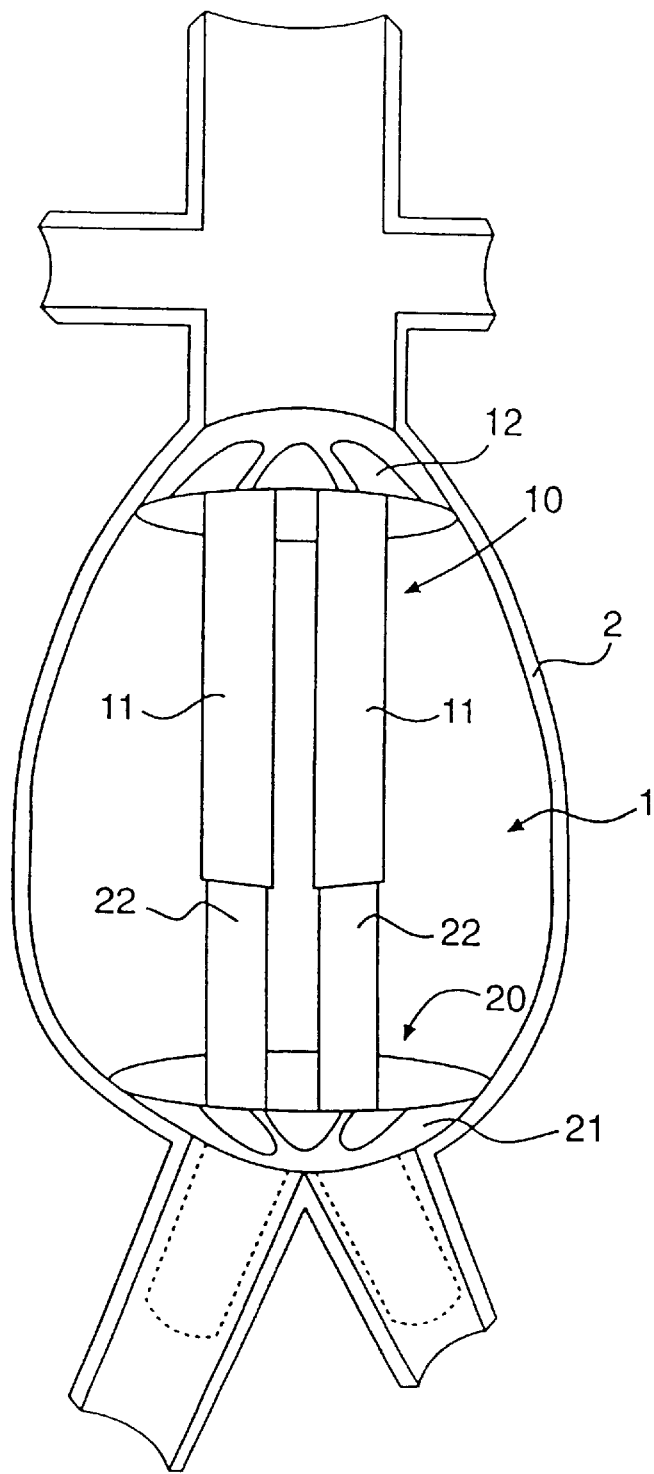
FIG. 3 is a perspective view of the prosthetic bifurcated tube graft and bifurcated cuff of FIG. 1 secured within the abdominal aorta.

FIGS. 1 and 3 depict an embodiment of the repair graft assembly of the present invention directed to a proximal graft assembly 10 and distal graft assembly 20 for repair of a vessel 1. The proximal graft assembly 10 and distal graft assembly 20 are secured to a wall 2 of the vessel 1 to exclude the aneurysm from the circulatory system of the patient. In the embodiment of the present invention, the proximal graft assembly 10 is a bifurcated tube graft.

The distal graft assembly 20 preferably comprises an attachment cuff 21. The attachment cuff 21 is sized to secure the distal graft assembly 20 to the wall 2 of the vessel 1 at the distal end of the vessel 1. The distal graft assembly 20 also comprises at least one graft attachment leg, tube or branch 22. The attachment cuff 21 is secured to the wall 2 of the vessel 1 out to the adventitia using a suitable fastener, described in detail below.

Figure 7:
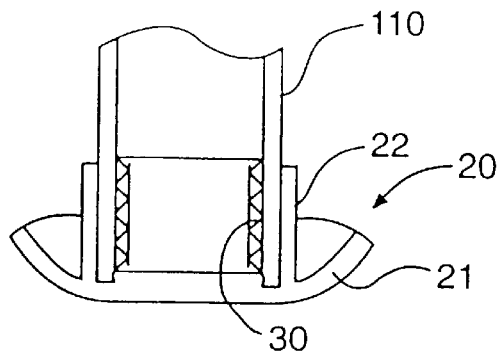
FIG. 7 is a perspective view of the connection between the prosthetic tube graft and the cuff.

The distal graft assembly 20 is positioned within the distal end of the vessel 1, as shown in FIG. 1 using a guide wire, not shown, that extends between and through both common iliacs. The attachment cuff 21 is then secured to distal end of the vessel 1 out to the adventitia using a repair apparatus, described below. After the attachment cuff 21 is firmly secured to the wall 2, attachment tubes 22 are invaginated to the position shown in FIG. 3. A proximal graft assembly 10 is then secured to the attachment legs 22 using suitable connectors, such as, a self-expanding stent 30, as shown in FIG. 7.

The bifurcated proximal graft assembly 10 comprises a pair of tubular legs 11. The tubular legs 11 are sized to be received within/without the graft attachment tubes 22. The bifurcated proximal graft assembly 10 may also comprise an attachment cuff 12 for attachment to the wall 2 of the vessel 1. The attachment cuff 12 has a similar structure to the attachment cuff 21 of attachment device 20. The tubular legs 11 are invaginated following the process of securing the attachment cuff 12 to the wall 2. The attachment legs 22 may be positioned within the tubular legs 11, as shown in FIG. 3. Alternatively, the tubular legs 11 may be positioned within the attachment legs 22, as shown in the embodiment of FIG. 6.

Figure 2:
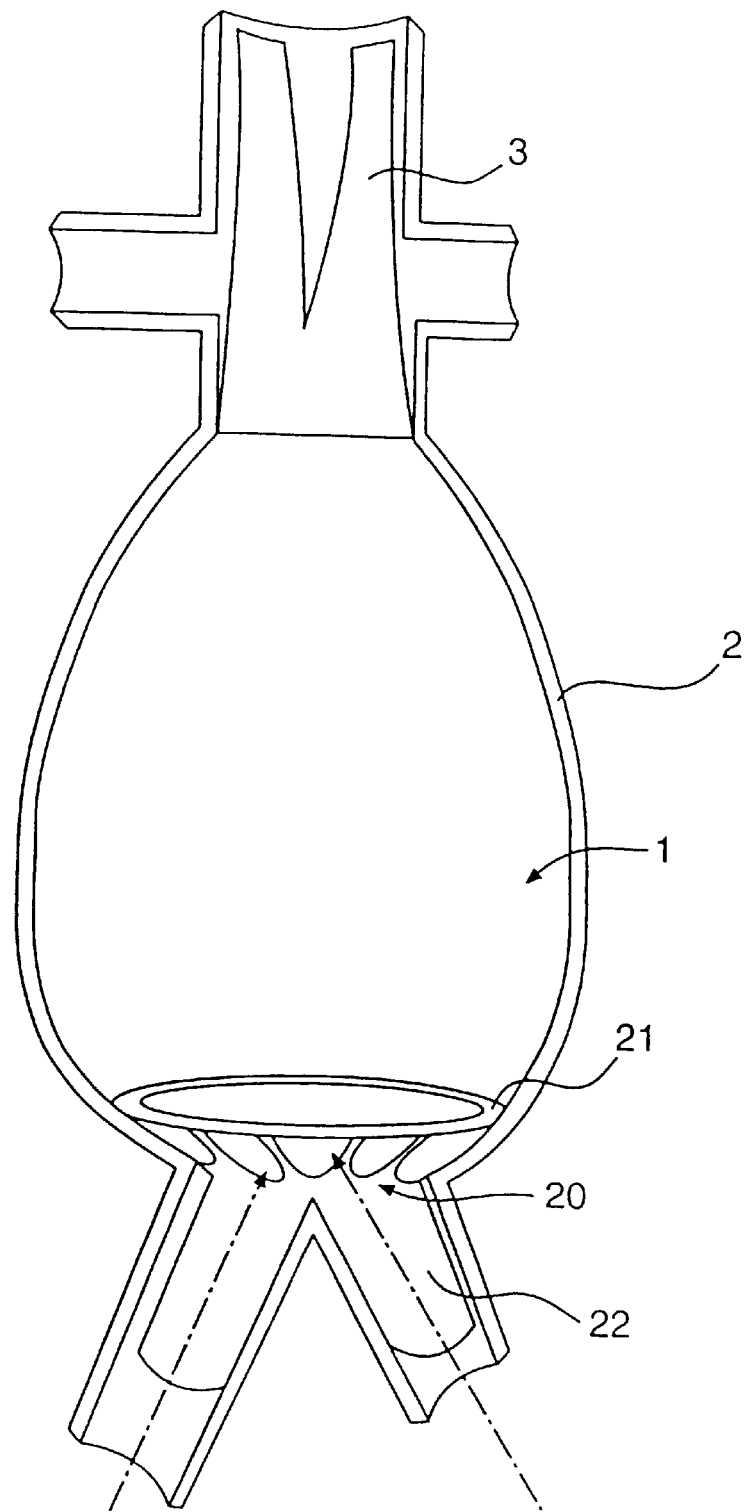
FIG. 2 is a perspective view of a prosthetic bifurcated tube graft and bifurcated cuff according to another embodiment of the present invention.
Figure 4:
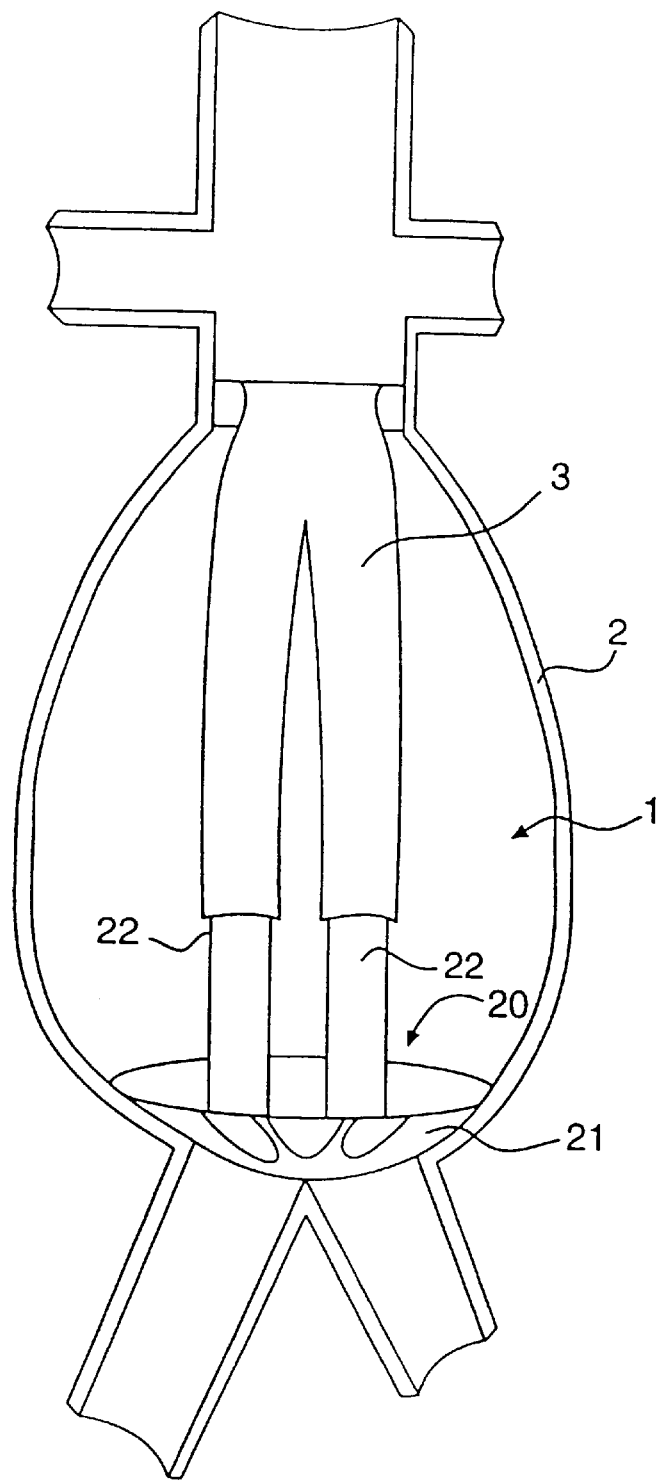
FIG. 4 is a perspective view of the prosthetic bifurcated tube graft and bifurcated cuff of FIG. 2 secured within the abdominal aorta.

It is also contemplated that the distal graft assembly 20 may be used with a standard tube graft 3, as shown in FIGS. 2 and 4. In this variation, the tube graft 3 is secured to the wall 2 of the vessel 1 while in an inverted position, as shown in FIG. 2 using fasteners, described below, and a self-expanding stent 30, if desired. The tube graft 3 is then invaginated and secured to the distal graft assembly 20, as described above. The benefit of the invagination of the graft 3 is that the fasteners securing the graft 3 to the vessel 1 are not in direct contact with the blood within the vessel 1. This will reduce the possible build up of thrombus at the point of attachment and thereafter the creation of emboli.

The proximal graft assembly 10 and distal graft assembly 20 will enable the creation of a cross sectional area ratio between the common iliacs and the distal aorta that exists only at childhood. The ratio may be 1.1 to 1.0. This ratio minimizes the reflected wave that is instrumental in the creation of plaque deposits at the distal bifurcation.

Figure 5:
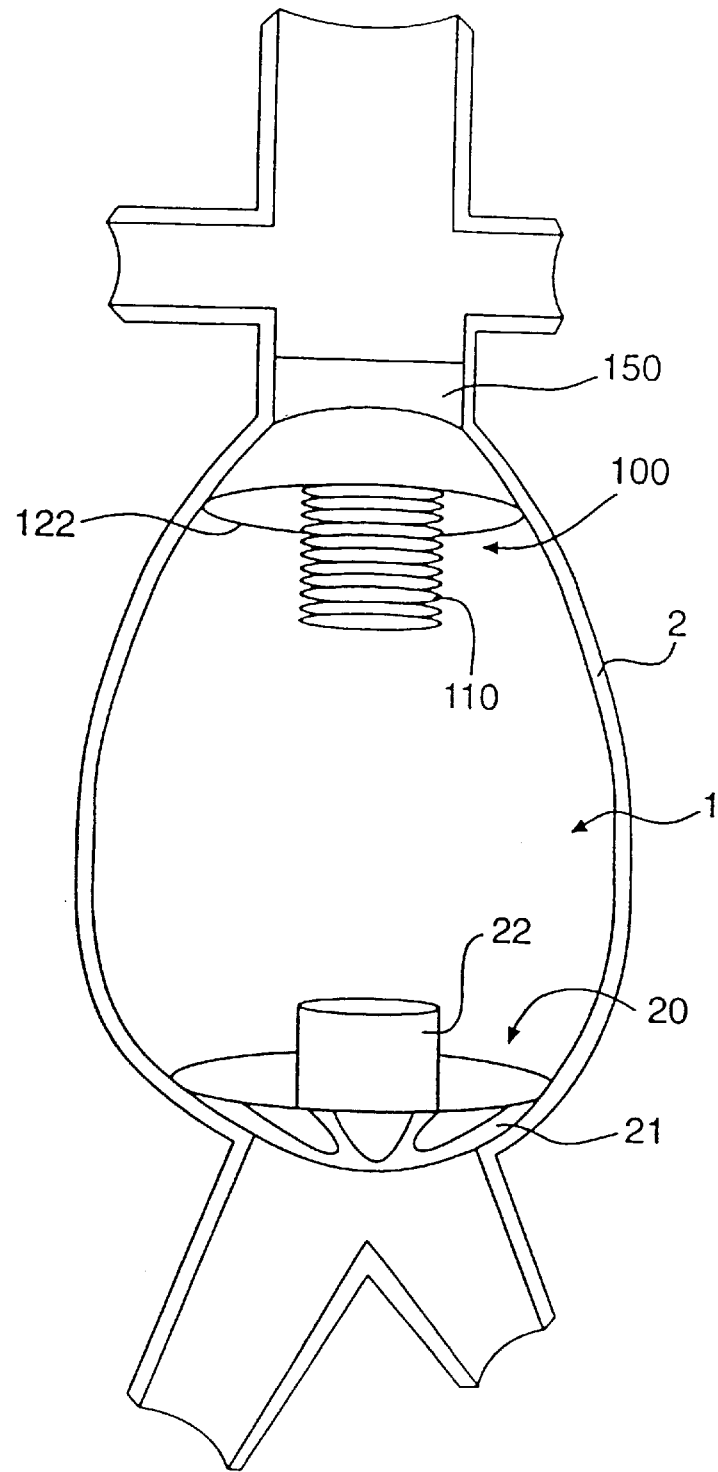
FIG. 5 is a perspective view of a prosthetic tube graft and cuff according to another embodiment of the present invention.
Figure 6:
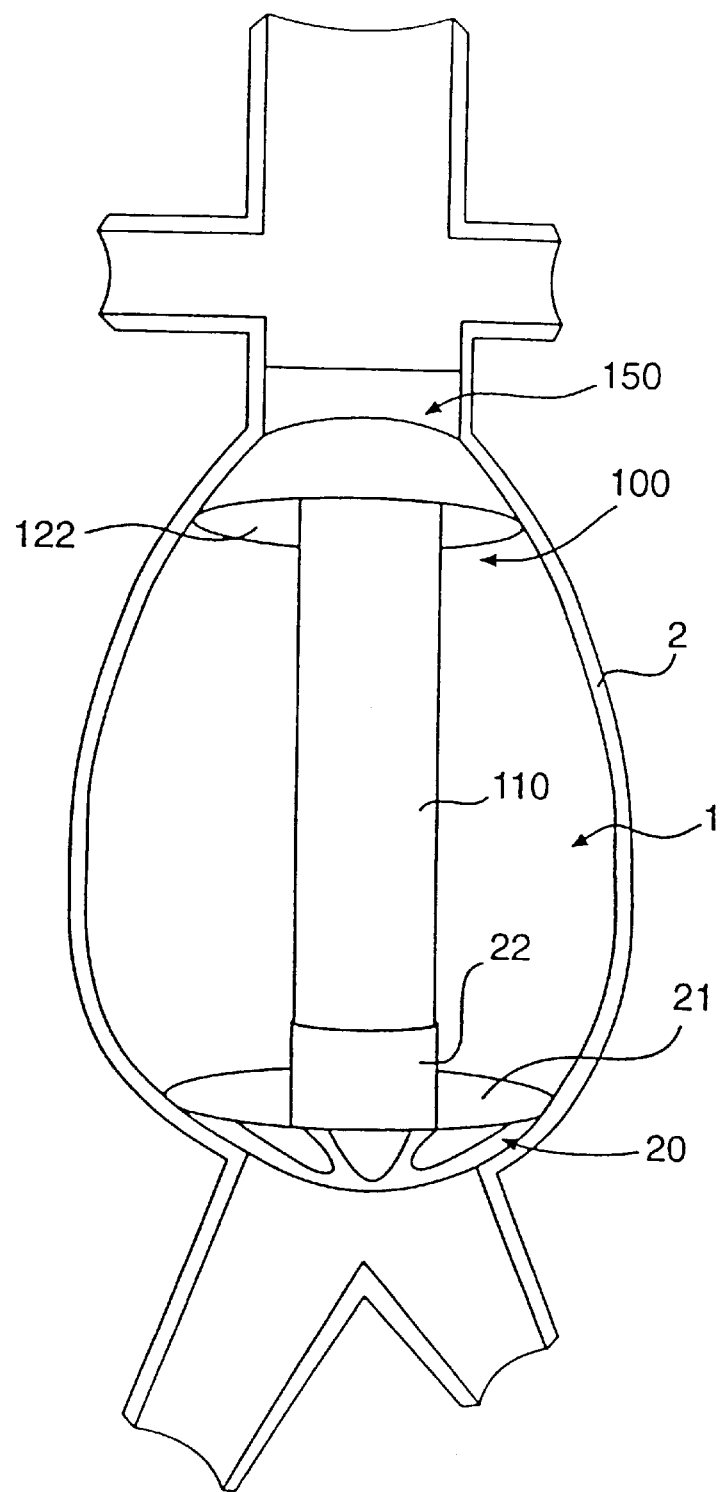
FIG. 6 is a perspective view of the prosthetic tube graft and cuff of FIG. 5 secured within the abdominal aorta.

FIGS. 5 and 6 depict another embodiment of a repair graft for repair of an abdominal aortic aneurysm 1 according to the present invention. The proximal graft assembly 100 is secured to a wall 2 of the abdominal aorta to exclude the aneurysm 1 from the circulatory system of the patient. The proximal graft assembly 100 is used in connection with the distal graft assembly 20, described above. In this embodiment, the distal graft assembly 20 comprises a single attachment leg or tube 22. The proximal graft assembly 100 comprises a tube graft assembly 110 for forming a passageway within the vessel 1.

Figure 11:
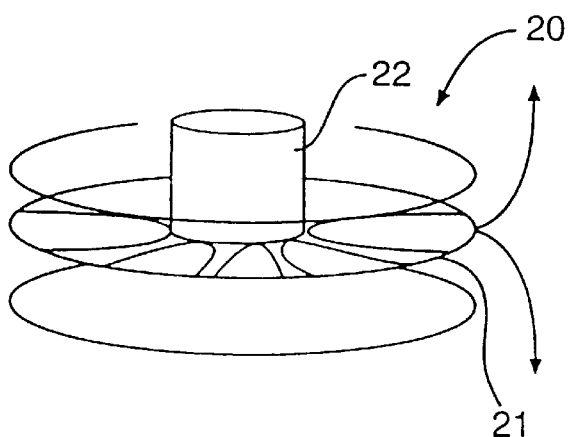
FIG. 11 is a perspective view of the flexible attachment cuff according to embodiments of the present invention.

The radially extending attachment cuff 121 provides a greater surface area for securing the proximal graft assembly 100 to the wall 2. Additionally, the radially extending portion 121 is flexible, which permits some positioning adjustment of the proximal graft assembly 100 in the event the size of the passageway within the abdominal aorta changes after the surgical procedure. FIG. 11 illustrates the flexibility of the attachment cuff 21 which is similar to attachment cuff 121. Like the embodiment of FIGS. 1 and 3, the proximal graft assembly 100 is secured to the vessel wall 2 in an invaginated manner, as shown in FIG. 5. After the attachment cuff 121 is secured to the vessel wall 2, the proximal graft assembly 100 is invaginated to the position shown in FIG. 6. The tubular leg assembly 110 is then secured to the distal graft assembly 20, as shown in FIG. 7. In a preferred embodiment, a self-expanding stent 30 is used to secure it to the attachment leg 22 of the distal graft assembly 20. The self-expanding stent 30 applies radial pressure against an inner surface of tube graft assembly 110 to secure the tube graft assembly 110 to the distal graft assembly 20.

The self-expanding stent 30 is a preferred method of securing the proximal tube assemblies 10 or 100 to the distal graft assembly 20. However, it will be apparent to those skilled in the art that various modifications and variations can be made in the construction and configuration of the present invention without departing from the scope or spirit of the invention. For example, surgical staples, sutures, avhesives or other methods may be used to secure the proximal graft assembly 10 to the distal graft assembly 20. Thus, it is intended that the present invention cover the modifications and variations of the invention, provided they fall within the scope of the appended claims and their equivalents.

As described above in connection with FIGS. 2 and 4, it is also contemplated that the distal graft assembly 20 may be used with a standard tube graft, not shown. The tube graft will also be secured to the wall 2 of the vessel 1 while in a cephalad position using any of fastener devices, described below, or a self-expanding stent 30. The tube graft is then invaginated and secured to the distal graft assembly 20, as described above.

Figure 8:
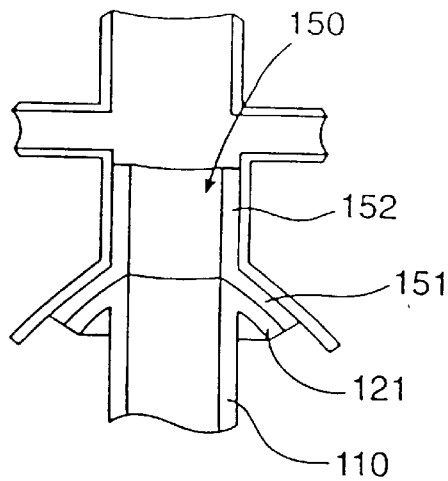
FIG. 8 is a side view of the prosthetic tube graft of FIG. 6 secured to a secondary cuff.
Figure 9:
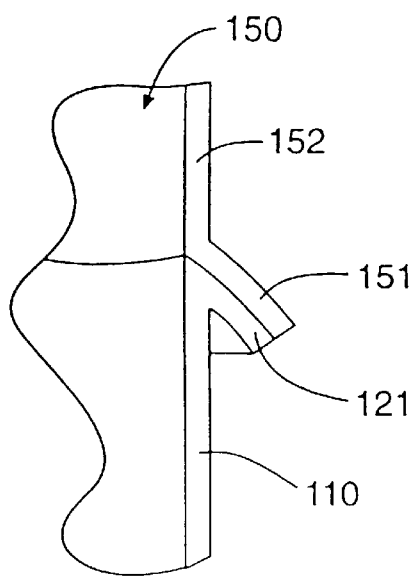
FIG. 9 is an exploded view of the connection between the prosthetic tube graft and secondary cuff as shown in FIG. 8.

FIGS. 8 and 9 depict a proximal attachment assembly 150 according to the present invention for securing the proximal graft assembly 10 or 100 to the proximal end of the vessel 1. It is preferred that the proximal attachment assembly 150 be used in connection with securing the proximal graft assemblies 10 or 100 to the vessel wall 2 according to embodiments of the present invention as shown, for example, in FIGS. 5, 6, 8 and 9. The proximal attachment assembly 150 comprises a cuff attachment portion 151 and a vessel attachment portion 152. The attachment cuff 12 or 121 is secured to the cuff attachment portion 151, by sewing, for example. The vessel attachment portion 151 is then secured to the vessel 1 using, for example, a fastener or a self-expanding stent 30 and fasteners, if necessary. Alternatively, the proximal attachment assembly 150 may be invaginated and secured to the vessel 1 in the manner described above in connection with FIGS. 2 and 4. The cuff attachment portion 151 and the attachment cuff 12 or 121 interact in a manner such that the proximal graft assembly 10 or 100 are not impacted by the expansion of the neck of vessel 1 after the surgical procedure.

Figure 10:
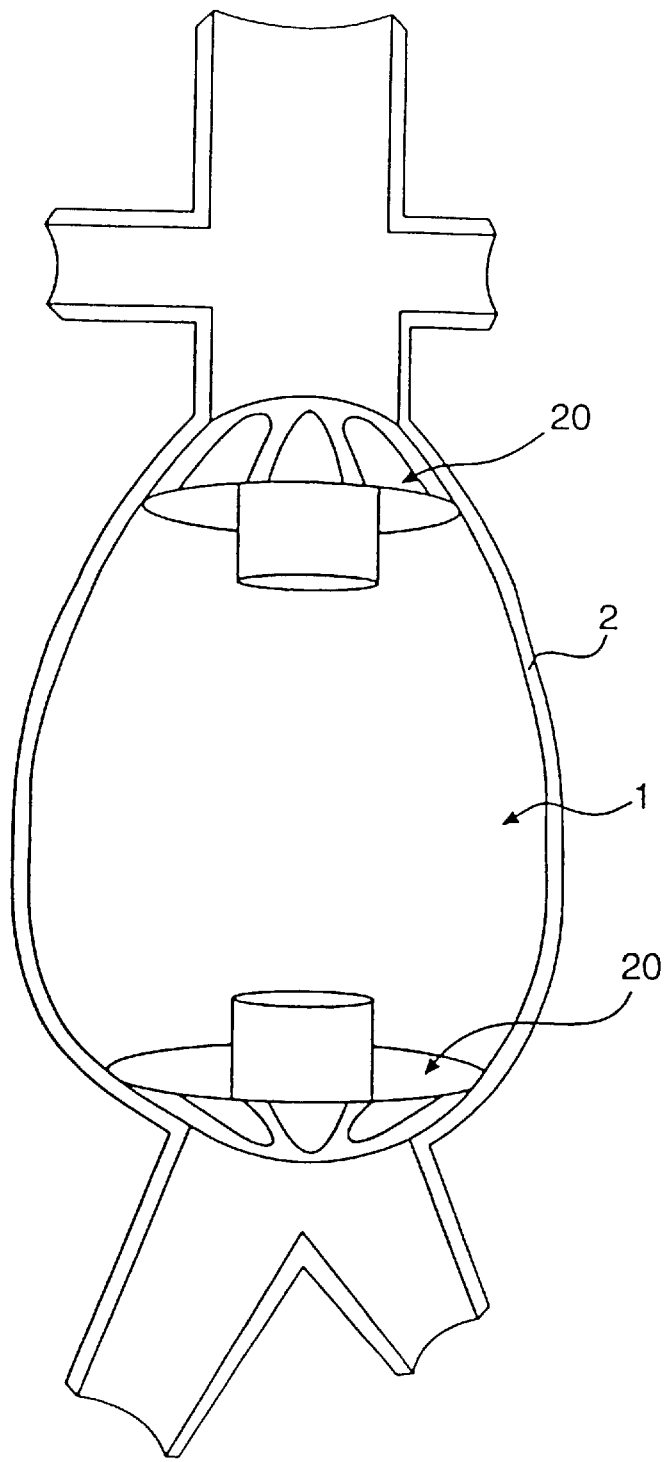
FIG. 10 is a perspective view of attachment cuffs according to another embodiment of the present invention.
Figure 12:
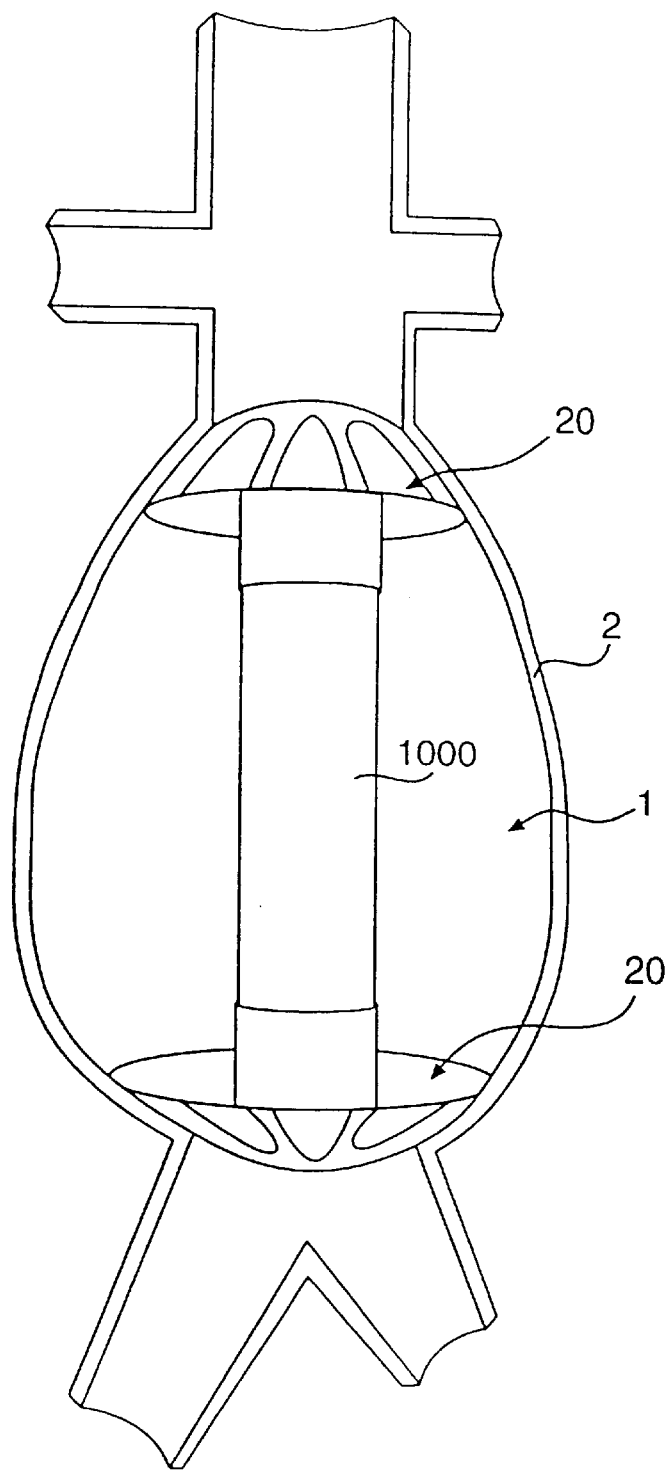
FIG. 12 is a perspective view of the attachment cuffs of FIG. 10 having a prosthetic tube graft secured between the attachment cuffs.

Another embodiment of the repair grafts according to the present invention is disclosed in FIGS. 10 and 12. The embodiment of FIGS. 10 and 12 utilizes a pair of distal graft assemblies 20, which are secured at the proximal and distal ends of the vessel. A proximal graft assembly 1000, which forms a passageway within the vessel 1 interconnects the distal graft assemblies 20. As described above, the proximal graft assembly 1000 is secured to the attachment legs 22 of the distal graft assemblies 20 using a self-expanding stent 30 or other suitable fastening means. The attachment legs 22 may be inserted in the proximal graft assembly 1000. Alternatively, the proximal graft assembly 1000 may be inserted in the attachment legs 22, as shown in FIG. 12.

The above described repair grafts facilitate repair of a vessel in a manner that is neither profile nor dimension dependent. This is especially helpful in view of the fact that the necks of the post-surgical aorta typically increases in size for approximately twelve months. The above-described repair grafts accommodate such expansion without allowing leaks or graft migration. The attachment cuffs are capable of accommodating dimensional changes in the necks of the abdominal aorta. Furthermore, the use of the distal graft assembly 20 permits distal attachment removing the need for iliac/femoral attachment.

In accordance with the present invention, detailing and assembly of the graft within the abdominal aorta creates a situation in which the fasteners are positioned outside the blood flow and are therefore not a focal point for thrombus creation. Both distal and proximal bifurcated grafts in accordance with the present invention may be strategically marked with radiopaque materials to enable their visual tracking and correct positioning prior to fixation within the aorta. A frieze/band of platinum oxide is vacuum deposited, photo deposited, silkscreened, or otherwise adhered to the graft material at the location of the tube end (proximal graft), tube end/halo transition (distal graft), and at the halo perimeter. Other noble metals such as gold, molybdenum and titanium may also be successfully used as marking material. Radiopaque wires or metal fragments have been woven or otherwise incorporated into grafts—the coating methods listed above, have not. The ring details previously discussed titanium or polymeric (suitably impregnated) are also radiopaque.

In the above described embodiments, the proximal graft assemblies 10, 100 and 1000, distal graft assembly, and proximal attachment assembly 150 are preferably formed from a twill weave, non-crimped polyester, Gore-Tex® or equivalent biocompatible material. It will be apparent to those skilled in the art that various modifications and variations can be made in the construction and configuration of the present invention without departing from the scope or spirit of the invention. For example, in the embodiments mentioned above, various other suitable materials such as, Dacron®, and other biocompatible graft materials may be used to form the repair grafts. Thus, it is intended that the present invention cover the modifications and variations of the invention, provided they fall within the scope of the appended claims and their equivalents.

The attachment cuffs may include a ring located at the perimeter. This ring may comprise a metal spring wound into holes cut in the cuff of a polymeric spring which is molded directly to the cuff. The ring serves to keep the cuff fully expanded during the attachment process of the graft to the vessel wall. The ring has no negative impact on the insertion process, described below.

Similar to other graft procedures, the proximal graft assemblies 10, 100, or 1000 according to the present invention require attachment to the wall 2 of the vessel. Often, it is necessary to attach the distal end of the graft into material which is routinely calcified and therefore difficult to penetrate. When paired with the absence of a distal neck in the vessel, the presence of the plaque has forced others to promote the use of a bifurcated graft in which the graft limbs are fastened by stents within the common iliac or femoral arteries. This procedure may potentially damage the femoral arteries. Furthermore, the presence of a graft and stent within the iliac or femoral arteries potentially restricts the flow of blood within the vessels. This is unnecessary when utilizing the repair grafts according to the present invention.

IntraVascular Angiography (IVA) Based Repair System

Reference will now be made in detail to embodiments of an apparatus according to the present invention for facilitating the repair of abdominal aortic aneurysms using above described grafts. An example of an intravascular Angiography based system is depicted in FIGS. 13–22.

Figure 20:
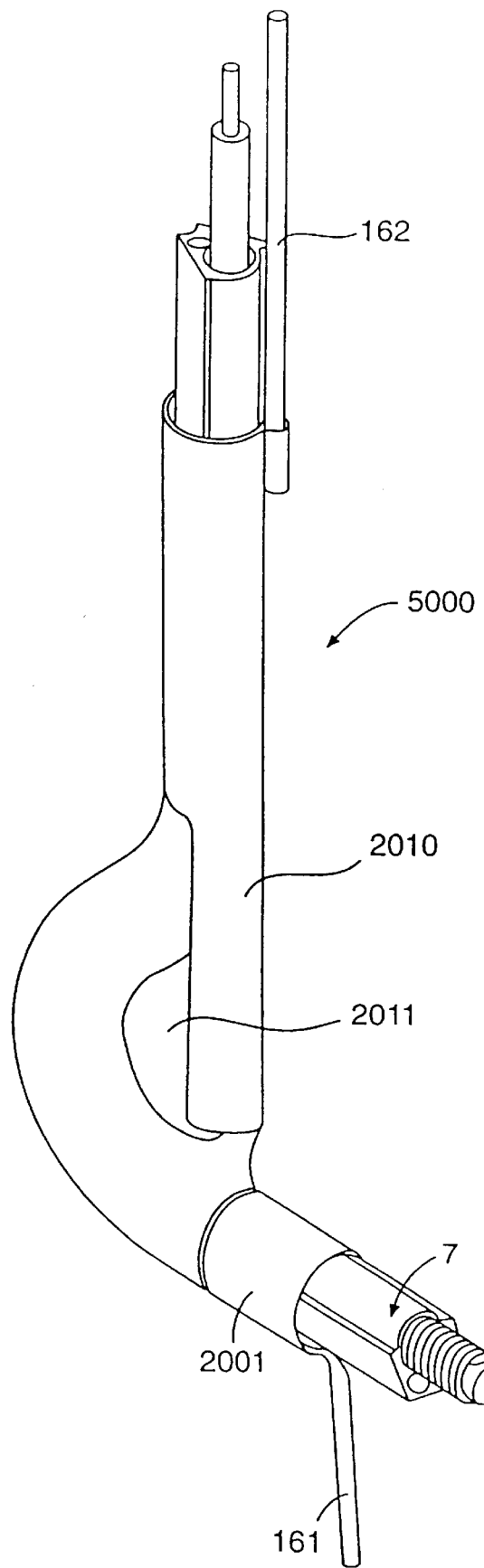
FIG. 20 is a perspective view of an IVA based repair system according to another embodiment of the present invention containing a penetration device and fastener cartridge according to the present invention.

The repair apparatus 5 comprises a housing 200 for alternately receiving a visualization apparatus 6 and a penetration apparatus 7, as shown in FIG. 20. It, however, is contemplated by the inventors of the present invention that the visualization apparatus 6 and penetration apparatus 7 may be combined into a single assembly within the repair apparatus 5. The housing 200 has a hollow construction, as illustrated in FIG. 14, which permits insertion of the visualization apparatus 6 or the penetration apparatus 7, described in detail below. The housing 200 is divided into two primary portions: static housing portion 210; and flexible housing portion 220. The housing 200 has a sufficient length such that it extends from the repair site within the vessel 1 through the appropriate or chosen artery to a point outside the patient.

The housing 200 has a hollow interior 211 to permit passage of one of the interchangeable apparatus 6 and 7. An inner surface of the hollow interior 211 comprises rotation prevention means 212 for properly orienting the interchangeable apparatus 6 and 7 within the housing 200. In a preferred embodiment, the rotation prevention means 212 is a ridge, as shown in FIG. 14, that extends along the inner surface of the hollow interior 211. It, however, will be apparent to those skilled in the art that various modifications and variations can be made in the construction and configuration of the present invention without departing from the scope or spirit of the invention. For example, the rotation prevention means 211 mentioned above, may be located at different radial positions within the housing and may also be a ridge, a groove, a plurality of grooves, or other devices capable of preventing rotation of the interchangeable apparatus 6 and 7 within the housing 200. Thus, it is intended that the present invention cover the modifications and variations of the invention, provided they fall within the scope of the appended claims and their equivalents.

Figure 13:
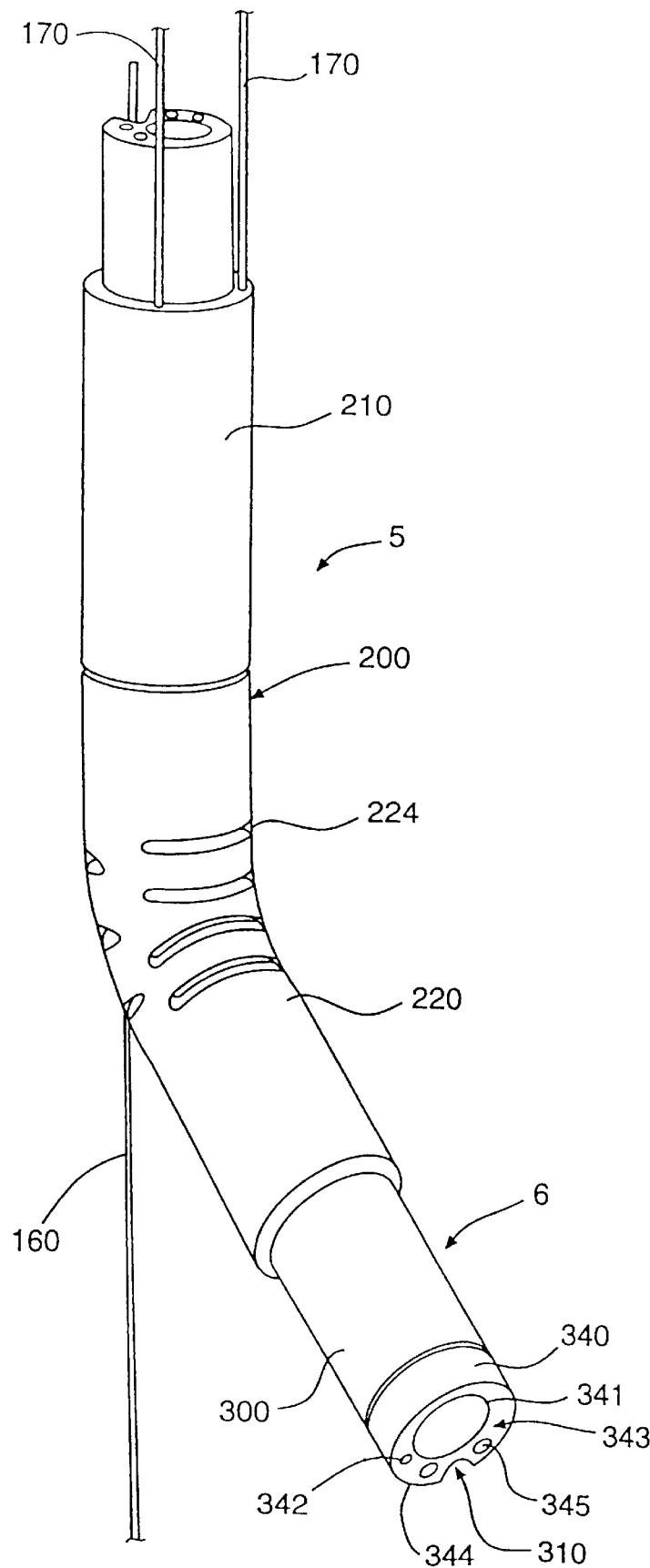
FIG. 13 is a perspective view of an IntraVascular Angiography (IVA) based repair system according to an embodiment of the present invention containing an embodiment of a visualization device according to the present invention.
Figure 17:
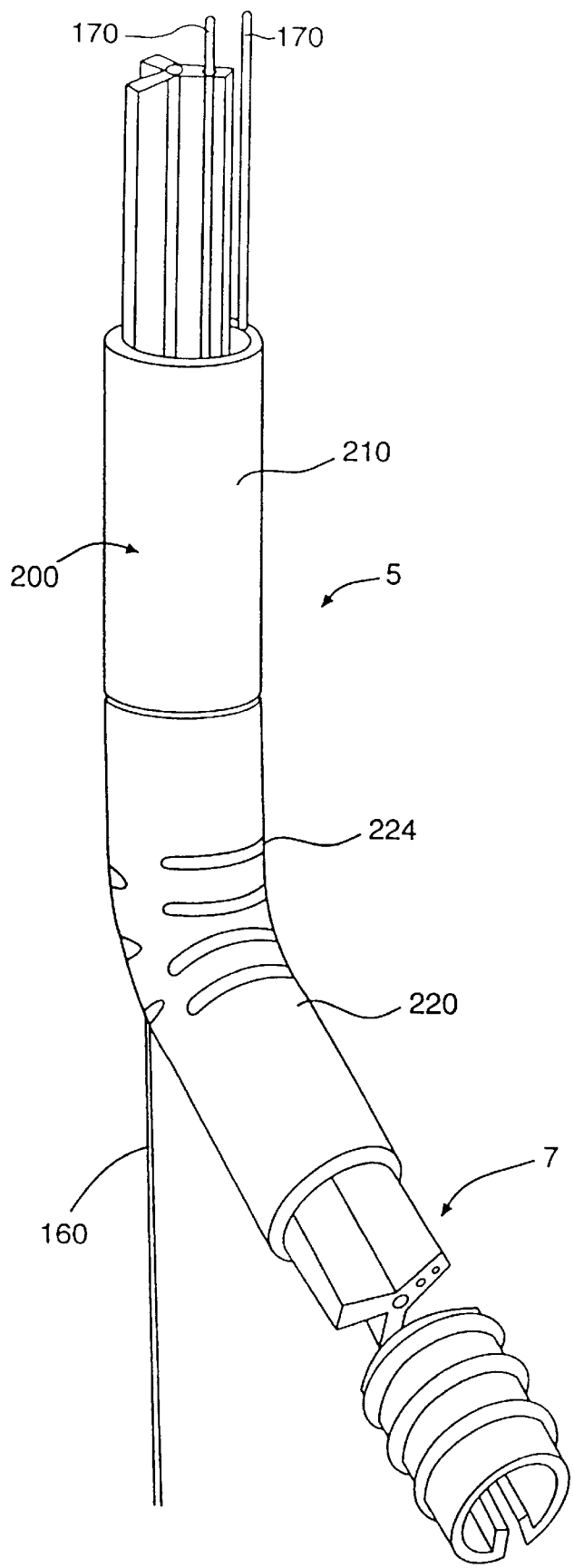
FIG. 17 is a perspective view of an IntraVascular Angiography (IVA) based repair system according to an embodiment of the present invention containing an embodiment of a penetration device according to the present invention and an embodiment of a fastener cartridge according to the present invention.

Positioned within the housing 200 is an apparatus guide means 214 for guiding the repair apparatus 5, as shown in FIGS. 13 and 17, within the vessel 1 during use. The guide means 214 preferably is a passageway or lumen extending within the housing wall through the static portion 210. A guiding means 160 cooperates with guide means 214 to guide the apparatus 5 during use. The guiding means 160 is preferably a guide wire which is capable of extending from the femoral artery to the axillary artery. In a preferred embodiment, the guide wire 160 is a filament (e.g., stainless steel, titanium or a Kevlar®). It, however, will be apparent to those skilled in the art that various other materials having similar properties of physical integrity, high strength, flexibility, and minimal thermal expansion may be used to form the guide wire 160. The guide wire 160 projects from the flexible housing portion 220 through an aperture 226 in the housing 200, as shown in FIG. 14.

Housing 200 also comprises an apparatus manipulation means 215 to aid in manipulating and orienting the apparatus 5 within the vessel 1 during the repair operation. The manipulation means 215 preferably comprises at least one passageway extending within the housing wall through the static housing portion 210 and terminating in the flexible housing portion 220. A manipulating means 170 cooperates with manipulation means 215 to guide the apparatus 5 during use. The manipulating means 170 is preferably comprises at least one guide wire that is capable of extending from outside the patient through the housing 200. The guide wires 170 extend through the manipulating means 215. In a preferred embodiment, the guide wires 170 are filaments (e.g., stainless steel, titanium or a Kevlar®). It, however, will be apparent to those skilled in the art that various other materials having similar properties of physical integrity, high strength and flexibility may be used to form the guide wires 170.

The guide wires of the manipulating means 170 terminate within the flexible housing portion 220. Operation of the manipulating means 170 results in the articulation of an end portion of the flexible housing portion 220. The guide wires 170 maintain the flexible housing portion 220 in an articulated position, as shown in FIGS. 13 and 16, such that the visualization apparatus 6 and the penetration apparatus 7 can be interchanged without altering the orientation of the repair apparatus 5 with respect to the surgical site.

The wall of the static housing portion 210 comprises an outer surface formed from silicone and an inner surface formed from Teflon®. It, however, will be apparent to those skilled in the art that various modifications and variations can be made in the construction and configuration of the present invention without departing from the scope or spirit of the invention. For example, the housing wall may be formed from a suitable polymer (e.g., Pebax®) or other material having similar properties including, but not limited to biocompatability, flexural strength, low coefficient of friction. Thus, it is intended that the present invention cover the modifications and variations of the invention, provided they fall within the scope of the appended claims and their equivalents.

The flexible housing portion 220 may be formed in a manner similar to static housing portion 210. For example, the housing may comprise an outer surface formed from silicon and an inner surface formed from Teflon®. It, however, will be apparent to those skilled in the art that various modifications and variations can be made in the construction and configuration of the present invention without departing from the scope or spirit of the invention. For example, the lining may be formed from a suitable polymer or other material having similar properties including, but not limited to biocompatability, flexural strength, low coefficient of friction. Alternatively, the flexible housing portion 220 may comprise a coiled metallic spring outer casing 224 that surrounds a lining. The lining may be formed from Teflon®. The coiled metallic spring outer casing 224 may be formed from a biocompatible stainless steel or titanium. Furthermore, the spring outer casing 224 may be formed from other suitable spring materials. It is not necessary that the outer spring casing 224 extend along the entire length of the flexible housing portion 220. Rather, the outer spring casing 224 may be positioned along the portion of the flexible housing portion 220 that is subject to bending. However, it is contemplated that an outer spring casing that extends along the entire length of the flexible housing portion 220 be within the scope of the present invention.

The flexible housing portion 220 and the static housing portion 210 are manufactured as separate components. It, however, will be apparent to those skilled in the art that various modifications and variations can be made in the construction and configuration of the present invention without departing from the scope or spirit of the invention. For example, the static housing portion 210 and the flexible housing portion 220 may be formed as a single component. In a preferred embodiment, the static housing portion 210 is permanently secured to the flexible housing portion 220. However, it is contemplated that the housing portions 210 and 220 may also be removably attached.

Figure 18:
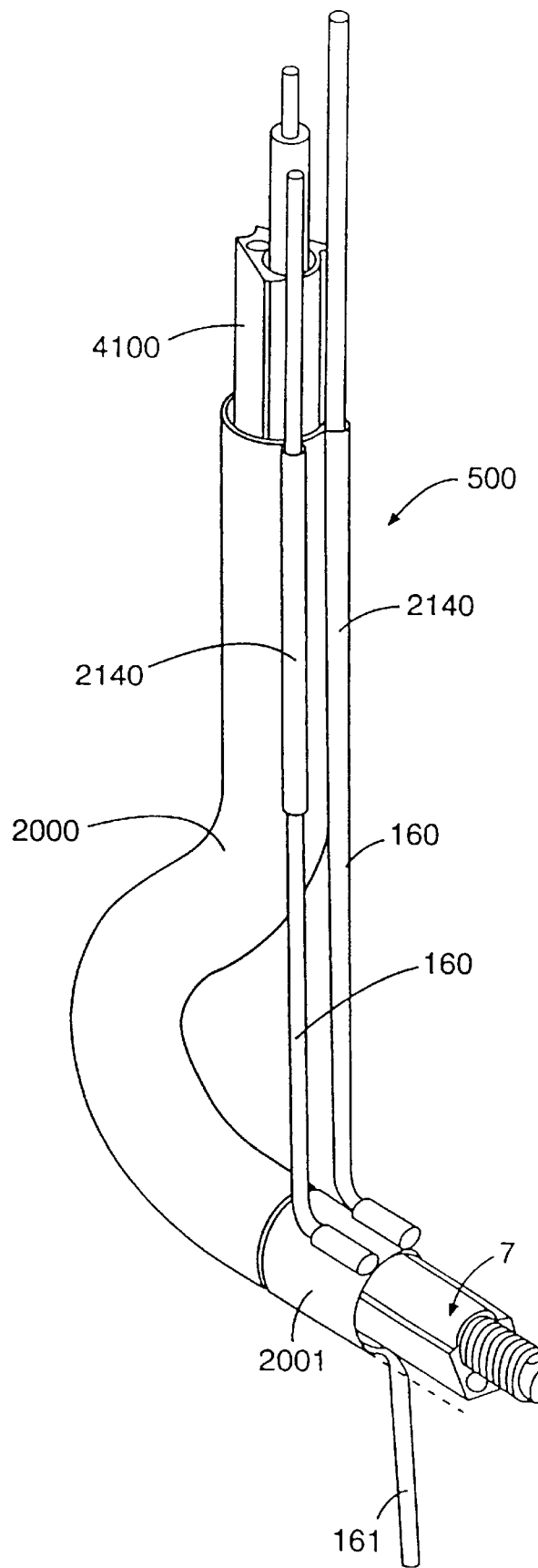
FIG. 18 is a perspective view of an IVA based repair system according to another embodiment of the present invention containing a penetration device and fastener cartridge according to the present invention.
Figure 19:
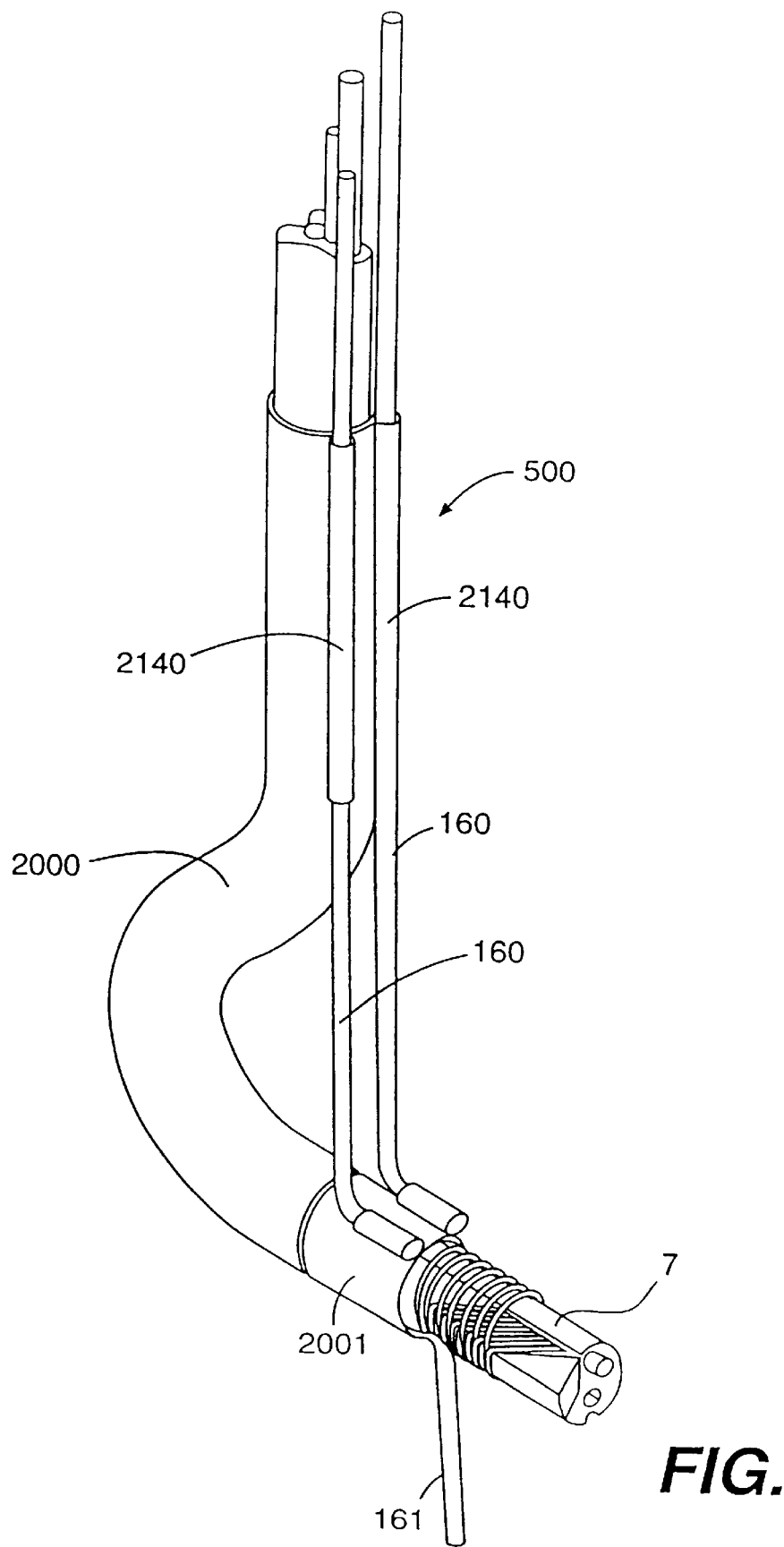
FIG. 19 is a perspective view of an IVA based repair system according to the embodiment of FIG. 18 containing a penetration device and fastener cartridge according to another embodiment of the present invention.

FIGS. 18 and 19 illustrates another repair apparatus 500 for alternatively receiving a visualization apparatus 6 and a penetration apparatus 7 according to another embodiment of the present invention. The repair apparatus 500 comprises a housing 2000 for alternatively receiving a visualization apparatus 6 and a penetration apparatus 7. The housing 2000 is flexible and has a sufficient length such that it extends from the repair site within the vessel 1 through the appropriate artery to a point outside the patient.

The housing 2000 is hollow, as described above in connection with housing 200, to permit passage of one of the interchangeable apparatus 6 or 7. The housing 2000 includes at least one guide means 2140 positioned at the exterior of the housing 2000 for guiding the repair apparatus 500 within the vessel 1 during use. The guide means 2140 preferably is a passageway extending along the exterior of the housing wall to a point adjacent the distal end 2001 of the housing 2000.

Guide wires 160 extend within the guide means 2140. The guide wires 160 extend from the end of guide means 2140 and are secured to the distal end 2001 of the housing 2000, as shown in FIGS. 18 and 19. Adjustment of the guide wires 160 manipulates the position of the repair apparatus 500 within the vessel 1. The above described arrangement permits a wide range of articulation of the repair apparatus 500 within the vessel 1.

An additional guide wire 161 is secured to the distal end 2001 of the housing 2000. The guide wire 161 extends through the vessel 1 and appropriate artery to permit the positional adjustment of the repair apparatus 500 within the vessel.

FIG. 20 illustrates another repair apparatus 5000 for alternatively receiving a visualization apparatus 6 and a penetration apparatus 7 according to another embodiment of the present invention. The repair apparatus 5000 comprises a flexible hollow housing 2010 and has a sufficient length such that it extends from the repair site within the vessel 1 through the appropriate artery to a point outside.

The housing 2010 includes at least one guide wire 162 extending along the exterior of the housing 2010, as shown in FIG. 20. The housing 2010 includes an inflatable portion 2011, located adjacent the distal end 2001. Inflation of the inflatable portion 2011 permits articulation of the repair apparatus 5000 within the vessel 1. A passageway, not shown, extends within the housing 2010 to permit inflation of the inflatable portion 2011 with a suitable fluid, such as, saline or suitable liquid polymers or air. An additional guide wire 161 is secured to the distal end 2001 of the housing 2010. The guide wire 161 extends through the vessel 1 and appropriate artery to permit the positional adjustment of the repair apparatus within the vessel.

The overall dimensions of the repair apparatus 5 allows axillary access. This previously was not possible. In this regard, the repair apparatus used in connection with the visualization apparatus 6 or penetration apparatus 7 is capable of being used in other surgical procedures not previously contemplated. The apparatus size permits insertion through an introducer sheath device 900, described below. The apparatus 5 may also be introduced into a vessel percutaneously. This procedure is less invasive and/or intrusive when compared to other repair surgical procedures.

IntraVascular Angiography (IVA) Visualization Apparatus

Reference will now be made in detail to embodiments of the interchangeable apparatus 6 and 7 for use with the repair apparatus 5 according to the present invention for facilitating the repair of abdominal aortic aneurysms. The visualization apparatus 6 will now be described in connection with FIGS. 13 and 15.

A visualization apparatus 6 may be inserted within the repair apparatus 5 to illuminate and permit real time direct viewing of the abdominal aorta to aid and the diagnosis and repair of the aneurysm. The visualization apparatus 6 is an intravascular endoscope based system that comprises a housing 300 for housing various illuminating and viewing components. The housing 300 is preferably formed as a conduit that is sized to slide within housing 200. In a preferred embodiment, the housing 300 is an extrusion of silicon, Teflon® or polymer or other material having similar properties.

The housing 300 extends through the hollow interior 211 of the housing 200. The housing 300 may comprise orientation means 310 for orienting the visualization apparatus 6 within the housing 200. The orientation means 310 cooperates with rotation prevention means 212. In a preferred embodiment, the orientation means 310 is a channel that extends along an outer surface of the housing 300. It, however, will be apparent to those skilled in the art that various modifications and variations can be made in the construction and configuration of the present invention without departing from the scope or spirit of the invention. For example, the orientation means 310 mentioned above may be located at different radial positions within the housing 300. The orientation means 310, may be a ridge, a groove, a plurality of grooves, or other devices that are complementary with the rotation prevention means 212 to prevent rotation of the visualization apparatus 6 within the housing 200.

As shown in FIG. 15, housing 300 comprises a plurality of passageways 311, 312, 313, 314, and 315 formed therein. The passageways 311, 312, 313, 314, and 315 extend along the entire length of the housing 300. Central passageway 311 is provided for the passage of optical viewing means 320 for viewing an abdominal aorta. In a preferred embodiment, the optical viewing means 320 is a fiber optic system. The system incorporates a fiber optic bundle. It, however, will be apparent to those skilled in the art that various modifications and variations can be made in the construction and configuration of the present invention without departing from the scope or spirit of the invention. For example, the optical viewing means 320 mentioned above, may be any flexible optical system that is sized for use in surgical applications. The optical viewing means 320 permits real time direct viewing of the area of repair in the vessel 1. The optical viewing means 320 may be connected to a video camera and monitor, not shown, that permits the surgeon to view the repair area. The images may be stored and recalled as desired by using either a video printer or video cassette recorder. The penetration apparatus 7 will be located at the same position as the visualization apparatus 6. The penetration apparatus 7 incorporates a radio opaque marker that will indicate the precise position of the penetration apparatus 7 on the monitor. This allows the surgeon to monitor and track the adjustments of the repair apparatus 5.

Peripheral illumination passageways 312 and 313 are provided for the passage of illuminating means 330 for illuminating the abdominal aorta for viewing by the optical viewing means 320. In a preferred embodiment, the illuminating means 330 is a fiber optic system including a fiber optic bundle. It, however, will be apparent to those skilled in the art that various modifications and variations can be made in the construction and configuration of the present invention without departing from the scope or spirit of the invention. For example, the illuminating means 330 mentioned above, may be any system that is sized for use in surgical applications and capable of illumination within the aorta. Although a pair of passageways are illustrated, it is contemplated that a single illumination passageway will provide sufficient illumination. Additionally, more than two passageways may also be provided.

Peripheral fluid inflow passageway 314 and peripheral fluid outflow passageway 315 are provided for the passage of fluid lens media to and from the visualization tip 340. The peripheral fluid inflow passageway 314 supplies a stream of optically clear fluid lens media from the visualization tip 340 in the area in front of the optical viewing means 320. A control means, not shown, may be incorporated into passageway 314 to control the flow volume and velocity of the fluid lens media to the visualization tip 340. The control means may be a valve or other suitable flow control devices.

The control means controls the optically clear fluid lens media such that blood within the aortic cavity and the fluid lens media are pressure balanced. As a result, blood that is typically within the aorta is temporarily diverted away by the fluid lens media to a point adjacent the area of the wall 2 to be viewed by the optical viewing means 320. The infusion of fluid lens media will dilute blood to an appropriate transparency in the immediate surgical site to exclude blood between the visualization tip 340 and the surgical site on the wall 2. This permits the surgeon to clearly view the wall 2 through the optical viewing means 320. In a preferred embodiment, the fluid lens is a transparent fluid to permit viewing of the wall 2. The fluid lens media may be a saline solution. It is preferred that the solution be used for a single application (i.e., it is not reused). Other media, such as $CO_2$ gas and Green Cross liquid fluorocarbon are contemplated to be within the scope of the present invention. The peripheral fluid outflow passageway 315 acts as a return duct for the fluid lens media within the aorta. Alternatively, the fluid lens media may then be filtered using an appropriate filtering means and recirculated using a pumping means through the peripheral fluid inflow passageway 314.

In a preferred embodiment, it is contemplated that the visualization apparatus 6 be used in combination with the introducer sheath devices 900, described below. The introducer sheath devices 900 and in particular the positioning assemblies 920 permit the isolation of a portion of the vessel during the repair procedure. Specifically, the positioning assemblies 920 within the common iliacs and femoral artery permit the control of blood within the vessel. With this arrangement, it is then possible to more readily divert blood away from a viewing area with the flow of fluid lens media from the fluid inflow passageway 314.

A visualization tip 340 is securely mounted to the end of housing 300 in a fluid tight manner. The tip 340 may be snap fitted or permanently mounted to the housing 300. It, however, will be apparent to those skilled in the art that various modifications and variations can be made in the construction and configuration of the present invention without departing from the scope or spirit of the invention. For example, the visualization tip 340 mentioned above, may be secured to the housing 300 by means other than the above described snap and permanent fittings. The visualization tip 340 may be formed by injection molding or other suitable manufacturing methods in silicone or similar polymer.

The visualization tip 340 comprises apertures 341, 342, 343, 344, and 345 that correspond to passageways 311, 312, 313, 314, and 315, respectively. Aperture 341 contains a lens positioned therein to facilitate viewing of the wall 2 with the optical viewing means 320. Apertures 342 and 343 may include windows therein whereby light from the illuminating means 330 passes through the windows to illuminate the wall 2, although it is not necessary. Apertures 344 and 345 act as gates for the peripheral fluid inflow passageway 314 and peripheral fluid outflow passageway 315. The aperture 344 may be inwardly tapered, such that the inside diameter of the aperture adjacent the inflow passageway 314 is greater than the diameter on the outer surface of the tip 340 to concentrate the stream of fluid lens media from the fluid inflow passageway 314. The aperture 345 may be outwardly tapered, such that the inside diameter of the aperture adjacent the inflow passageway 315 is less than the diameter on the outer surface of the tip 340. It is contemplated that the tip 340 is optional.

Penetration Apparatus

Figure 21:
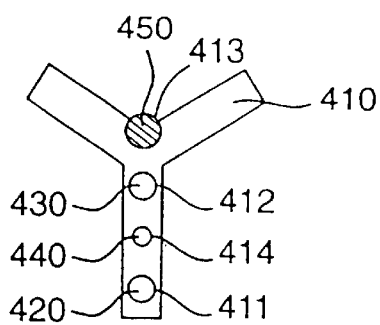
FIG. 21 is an end view of the penetration device according to an embodiment of the present invention.
Figure 22:
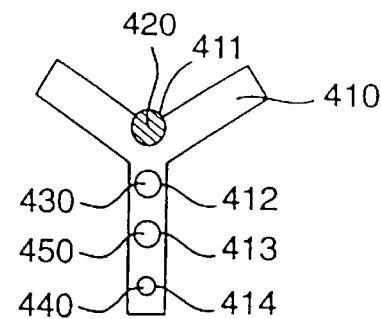
FIG. 22 is an end view of the penetration device according to another embodiment of the present invention.

A penetration apparatus 7 will now be described in connection with FIGS. 17–25. The penetration apparatus 7 may be inserted within the repair apparatus 5, 500, 5000, as shown in FIGS. 17–20, for fastening a repair graft to the vessel wall 2. The penetration apparatus 7 comprises several components for fastening a repair graft including penetration means 420, secondary penetration means 430, tracking means 440 and insertion means 450. The penetration apparatus 7 comprises housing 410 for housing the penetration means 420, secondary penetration means 430, tracking means 440 and insertion means 450. In a preferred embodiment, the housing 410 has a thin walled tri-limbed profile, as shown in FIGS. 19, 21, and 22. In a preferred embodiment for increased flexibility, the housing 410 is positioned within the repair apparatus 5 such that two of the three limbs of the housing 410 are spaced from the side of housing 200 containing the guide wire 160. It, however, will be apparent to those skilled in the art that various modifications and variations can be made in the construction and configuration of the present invention without departing from the scope or spirit of the invention. For example, the housing 410 mentioned above, may have more than three limbs. Alternatively, the housing 410 may be cylindrical having a plurality of inwardly projecting limbs. An alternative configuration for housing 4100 is depicted in FIGS. 18 and 20. The housing 4100 comprises a central passageway 4110 containing penetration means 420. Additional passageways 4210 and 4130 are provided for other components such as secondary penetration means, tracking means and insertion means.

The housing 410 is preferably formed from an extrusion of silicone, Teflon®, or polymer having similar properties. Housing 410 comprises a plurality of passageways 411, 412, 413, and 414, formed therein as shown in FIG. 21. An alternative arrangement is shown in FIG. 22. The passageways 411, 412, 413, and 414 extend along the entire length of the housing means 410. Primary passageway 411 is provided for the passage of the penetration means 420. The penetration means 420 is provided to create a treatment specific hole in the wall 2 of the abdominal aorta for securing the graft thereto with a suitable fastener device, described below. The penetration means 420 penetrates the potentially calcified vessel wall 2 to securely fasten the repair graft to the wall 2. The penetration means 420 may be either a laser penetrating device or a piezoelectric penetrating device. It, however, is contemplated by the inventors of the present invention that other penetration means including but not limited to $CO_2$ penetration, micro electromechanical systems, and intraluminal suturing are considered to be within the scope of the present invention. The laser penetrating device 420 preferably is an IR fiber optic based system using laser energy to create treatment specific holes in the aorta wall 2. The fused silica/quartz fibers that are utilized are in the 200–600 micron size range. Suitable lasers comprise but are not limited to an acousto optical laser having a wavelength of about 1.35 $\mu$m, and a Holmium-Yag laser having a wavelength of about 2.1 $\mu$m. The selected wavelength allows transition of laser energy through the fiber in the passageway 411. The laser fiber will be in direct contact with the surgical site such that the fiber projects from the end of the housing 410. It is contemplated that a single, or tri-pronged hole pattern will be created using penetration means 420 and secondary penetration means 430.

The piezoelectric penetrating device preferably is a catheter based system, which utilizes acoustic vibrations to create treatment specific suture holes to aid in graft/tissue attachment. The piezoelectric penetrating device applies an "acoustic wave" effect to create holes in the graft and vessel wall. In this variation, the passageway 411 preferably contains a super elastic titanium catheter, in rod or tube form, which enables transmittance of energy through the sometimes tortuous vessels to the surgical site. The catheter will be in direct contact with the surgical site such that the catheter projects from the end of the housing 410 into the formed treatment specific hole. The secondary penetration means 430 creates one or more temporary hole(s). The piezo-electronic device preferably operates at a frequency of 20 KHz. Other frequencies, both higher and lower, are contemplated to be within the scope of the present invention. The primary penetration means 420 is coaxial with the fastener devices such that the fastener devices may be inserted through the treatment specific hole created by the primary penetration means 420.

Secondary passageway 412 is provided for the passage of the secondary penetration means 430. The secondary penetration means 430 is also provided to create one or more temporary holes in the vessel wall 2, in a manner similar to the primary penetration means 420. Similarly, the secondary penetration means 430 may be either a laser penetrating device or a piezoelectric penetrating device, as described above in connection with the penetration means 420. The secondary penetration means 430 serves to anchor and orient the penetration apparatus 7 while a fastener is inserted within the treatment specific hole formed by the primary penetration means 420. After the secondary penetration means 430 is removed, the temporary holes will seal with blood that will coagulate.

Passageway 413 is provided within the housing 410 for passage of the insertion means 450, described below. Passageway 414 is provided within the housing means 410 for passage of the tracking means 440. In a preferred embodiment, the tracking means 440 is a radiopaque marker, which is utilized for the purpose of identifying the location of the penetration apparatus 7 within the image on the monitor. It, however, will be apparent to those skilled in the art that various modifications and variations can be made in the construction and configuration of the present invention without departing from the scope or spirit of the invention. For example, the tracking means 440 mentioned above, may be a tip-tracking device or a fiber optic aiming beam.

Figure 23:
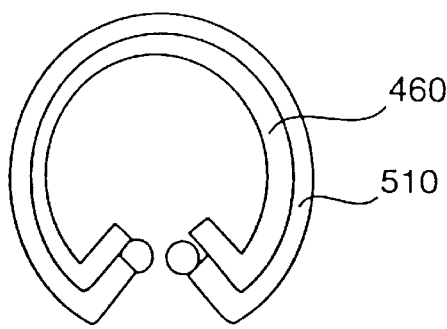
FIG. 23 is an end view of the fastener cartridge according to the embodiment of FIG. 17.

Insertion means 450 for securing the repair graft to the wall 2 during repair of the aneurysm will be described in connection with FIG. 24. The insertion means 450 preferably comprises a mechanism that drives an individual fastener from a fastener cartridge 460, shown in FIGS. 17 and 23, into and through the treatment specific holes created by the penetration means 420 in the repair graft and wall 2. The fastener cartridge 460 is capable of holding a plurality of fasteners such that more than one fastener may be sequentially displaced from the cartridge 460 to secure the repair graft to the abdominal aorta wall 2. Fastener cartridge 460 is preferably detachably connected to housing 410. The fastener cartridge 460 is a hollow housing, as shown in FIG. 23, preferably formed of injection molding HDPE or Liquid Crystal, manufactured by the RTP Co. of MN. The penetration means 420 and 430, the tracking means 440 and the insertion means 450 are appropriately accommodated within the interior of the cartridge structure 460. The cartridge 460 is positioned about the housing 410.

Figure 24:
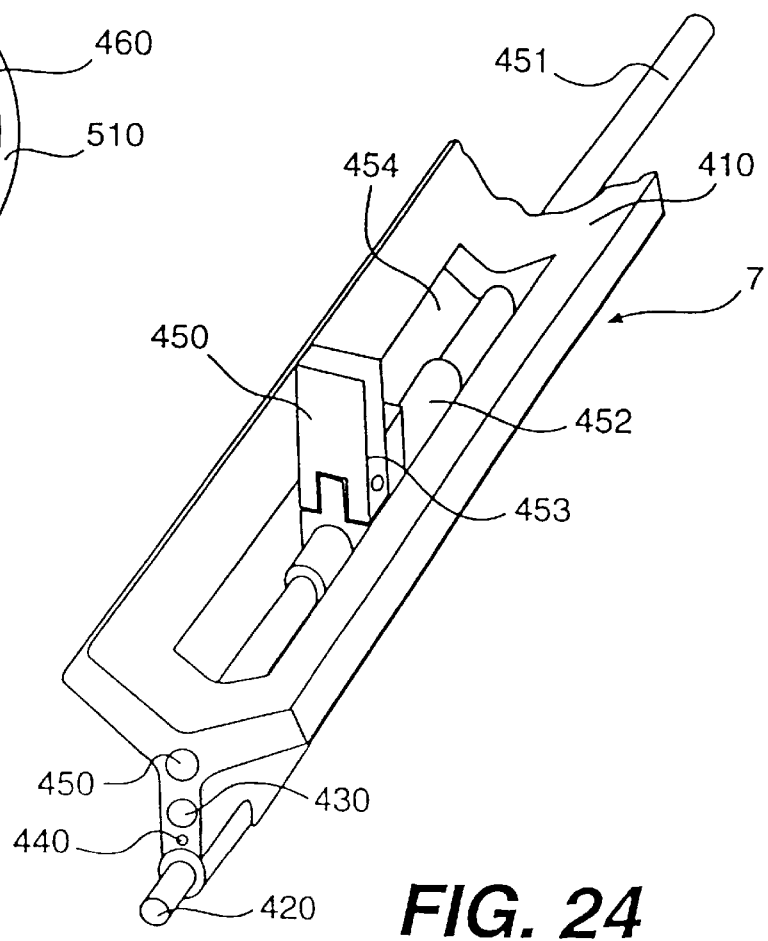
FIG. 24 is a perspective view of an advancing mechanism of a penetration device according to an embodiment of the present invention.

The insertion means 450 illustrated in FIG. 24 comprises a driving means 451 for driving the fastener devices to secure the repair graft to the vessel wall 2. A gear 452 and fastener advancing means 453 are positioned within an opening 454 in housing 410. In a preferred embodiment, the gear 452 is a worm gear. However, other suitable gear assemblies are contemplated to be within the scope of the present invention. The gear 452 is connected to the driving means 451. The fastener advancing means 453 interacts with the gear 452 to advance a fastener device to secure the repair graft to the vessel wall 2. In a preferred embodiment, the fastener advancing means 453 is an internally geared drive plate assembly. The drive plate assembly may be capable of limited angular adjustment. Operation of the insertion means 450 is controlled by a control device, not shown, such that upon actuation by the control device, the fastener advancing means 453 is advanced to eject a fastener device from fastener cartridge 460. Alternatively, the insertion means 450 may be hand operated. The insertion means 450 is used, for example, in the embodiment illustrated in FIG. 19.

Figure 25:
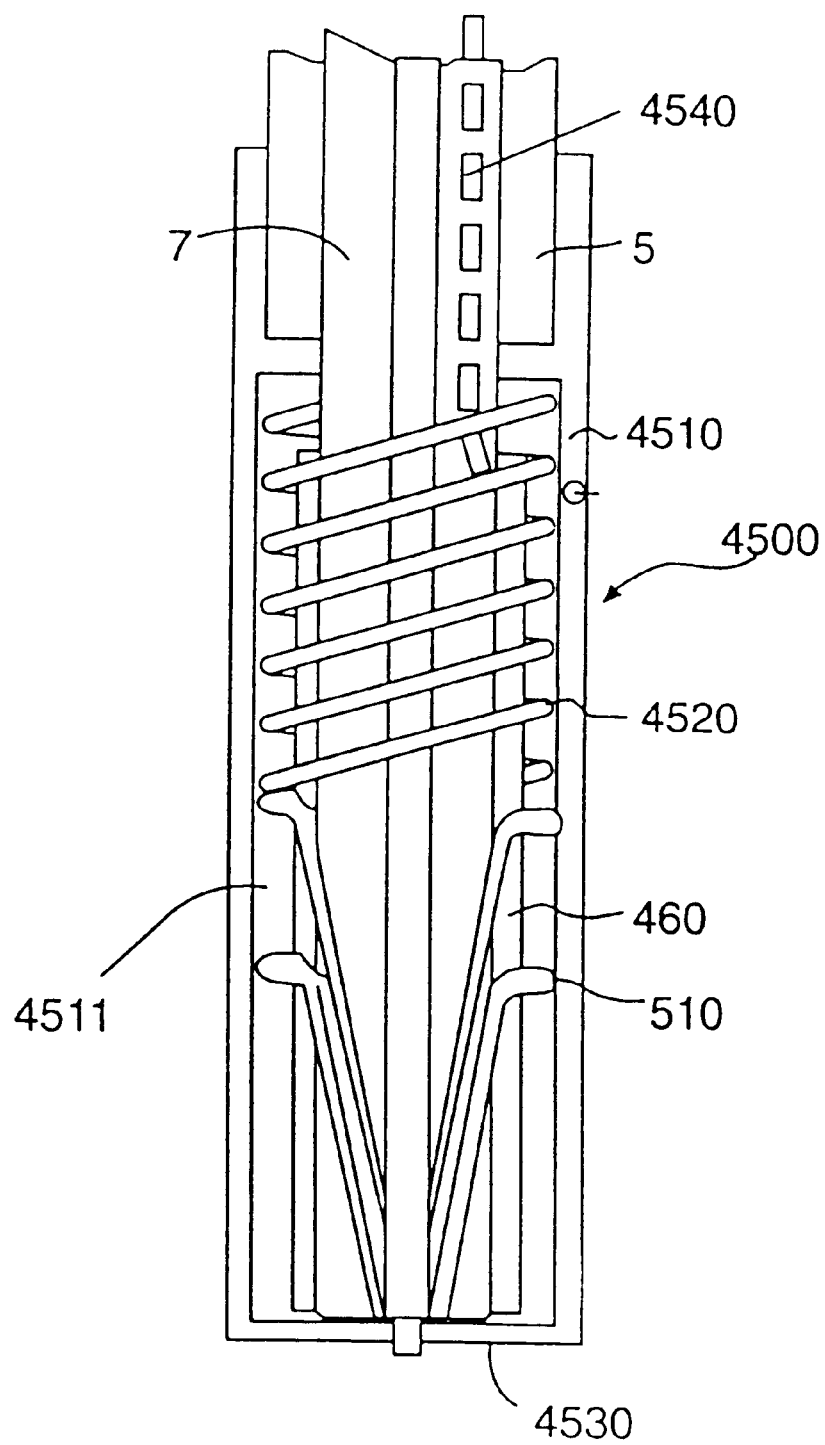
FIG. 25 is a schematic view of another advancing mechanism of a penetration device and fastener cartridge according to another embodiment of the present invention.

Another embodiment of the insertion means 4500 is illustrated in FIG. 25. An insertion cartridge 4510 is secured to the distal end of the repair apparatus 5. The insertion cartridge 4510 may be snap fitted to the housing 200. The insertion cartridge 4510 comprises a cavity 4511. A spring means 4520 is positioned within the cavity 4511. A fastener cartridge 460 is also located within the cavity 4511. An opening 4530 is located at one end of the insertion housing 4510. The housing 410 of the penetration apparatus 7 normally prevents the spring means 4520 from ejecting a fastener device through the opening 4530. The insertion means 4500 comprises retraction means 4540 which retracts the housing 410 away from the opening 4530 which permits the fastener to be ejected into the treatment specific hole created by the primary penetration means 420. The retraction means 4540 may be a cable that acts to retract the housing 410 away from opening 4530. The release of the retraction means 4540 causes the housing 410 to return to the position adjacent the opening 4530 to prevent the discharge of a subsequent fastener device.

It is contemplated that various changes, variations and modifications can be made to the penetration apparatus in accordance with the present invention. For example, the above-described penetration means can be replaced with an energy source to provide energy to heat the fasteners described in connection with FIGS. 60–72.

IntraVascular UltraSound (IVUS) Repair System

Reference will now be made in detail to preferred embodiments of an apparatus according to the present invention for facilitating the repair of abdominal aortic aneurysms using above described repair grafts. An example of an intravascular ultrasound based system is depicted in FIGS. 26–29.

Figure 28:
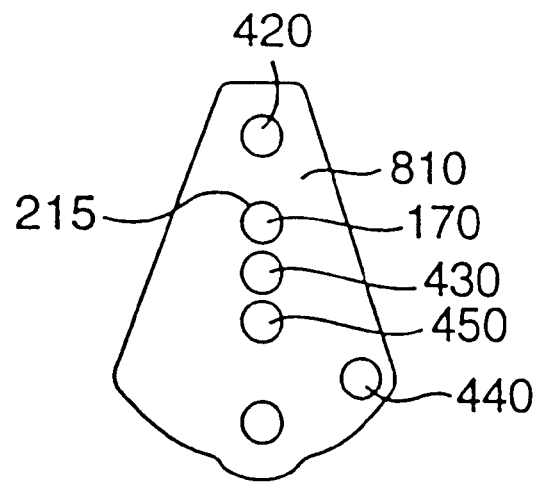
FIG. 28 is a cross sectional view of a housing according to an embodiment of the present invention.

The repair apparatus 50 comprises housing 800. The housing 800 comprises a major guide wire portion 810, a cross-section of which is shown in FIG. 28, a spacer portion 820, and a minor guide wire portion 830.

Positioned within the housing 800 is an apparatus guide means 214 for guiding the repair apparatus 50 within the vessel 1 during use. The guide means 214 preferably is a passageway or lumen extending the length of the housing 800 through major guide wire portion 810, the spacer portion 820, and the minor guide wire portion 830. A guiding means 160 cooperates with guide means 214 to guide the apparatus 50 during use. The guiding means 160 is preferably a guide wire which is capable of extending from the femoral artery to the axillary artery. In a preferred embodiment, the guide wire 160 is a filament (e.g., stainless steel, titanium or Kevlar® cable). It, however, will be apparent to those skilled in the art that various other materials having similar properties of physical integrity, high strength, flexibility, and minimal thermal expansion may be used to form the guide wire 160.

Housing 800 also comprises an apparatus manipulation means 215 to aid in manipulating and orienting the penetration apparatus 700 within the vessel 1 during the repair operation. The manipulation means 215 preferably comprises at least one passageway extending within the housing 810. The manipulation means 215 mates with complimentary passageways formed in housing 710. A manipulating means 170 cooperates with manipulation means 215 to guide the apparatus 50 during use. The manipulating means 170 is preferably comprises at least one guide wire that is capable of extending from outside the patient through the housings 810 and 710. The guide wire 170 extends through the manipulating means 215. In a preferred embodiment, the guide wire 170 is a super elastic metal filament. It, however, will be apparent to those skilled in the art that various other materials having similar properties of physical integrity, high strength and flexibility may be used to form the guide wire 170.

Figure 26:
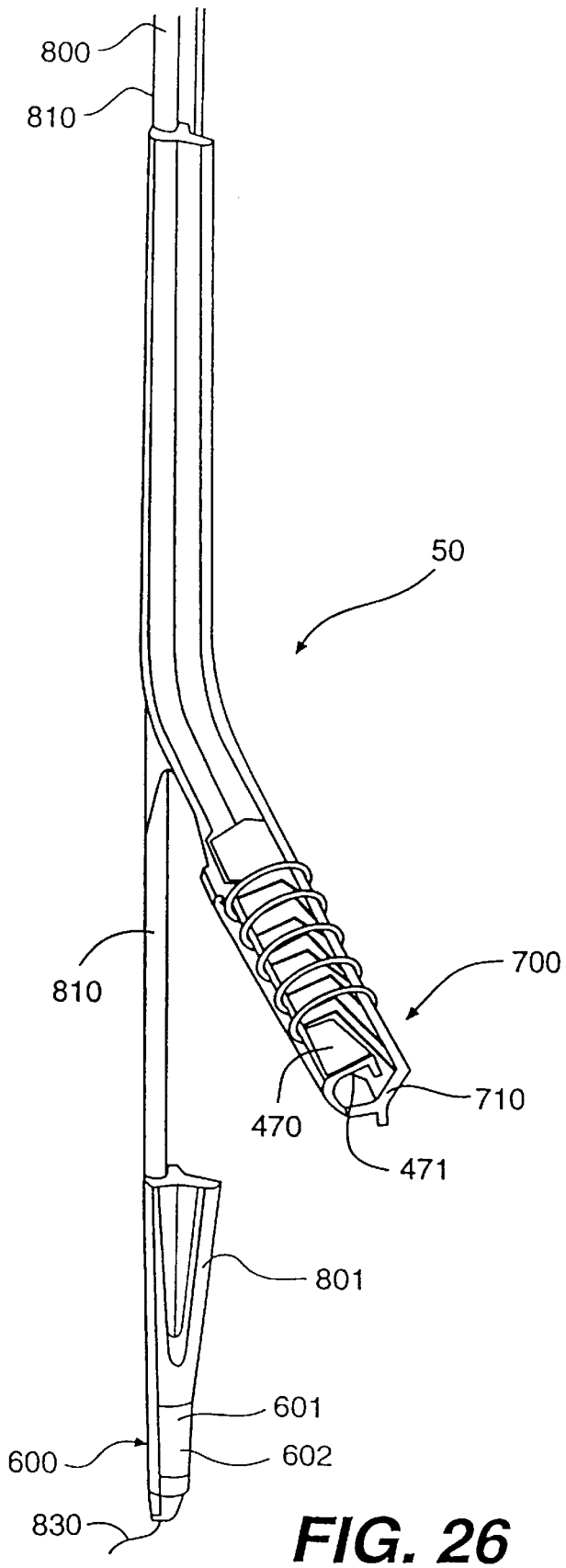
FIGS. 26 and 27 are perspective views of an IntraVascular UltraSound (IVUS) based repair apparatus according to another embodiment of the present invention containing a visualization device and a penetration device.

Operation of the manipulating means 170 results in the articulation of an end portion of the housing 710. The guide wire 170 maintains the housing 710 in an articulated position, as shown in FIG. 26, during the repair operation.

Figure 27:
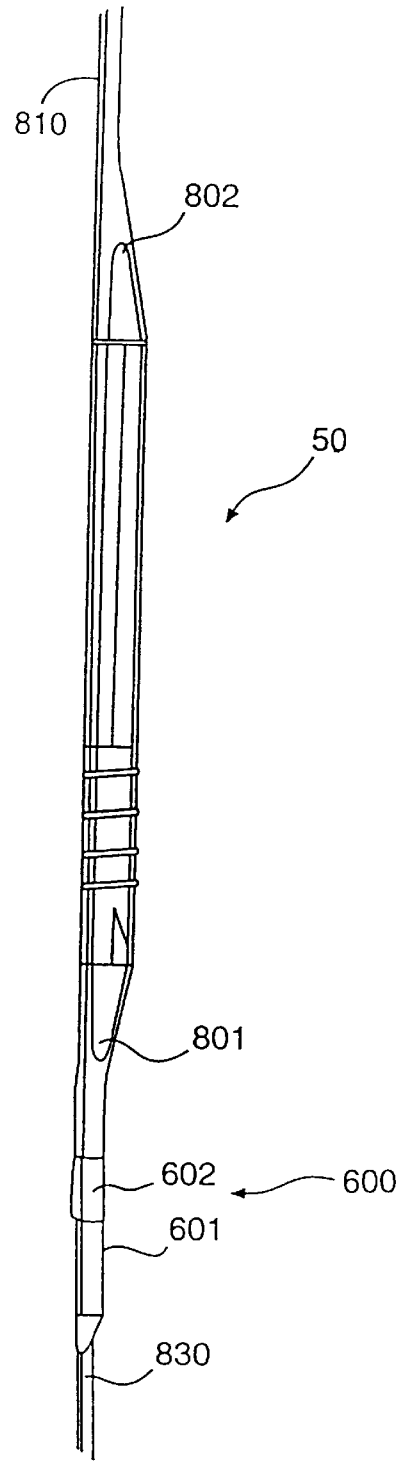
Figure 29:
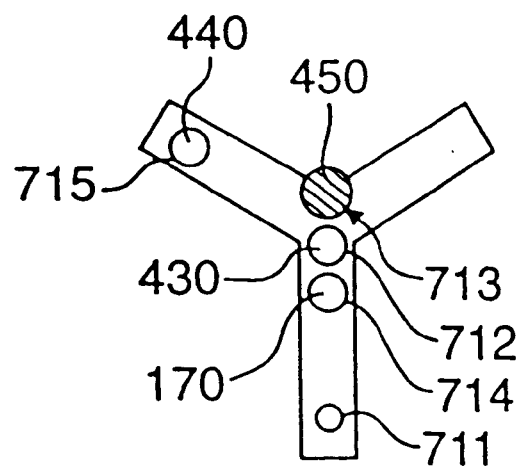
FIG. 29 is an end view of a penetration device depicted in FIG. 26.

The penetration apparatus 700 will now be described in connection with FIGS. 26–29. The penetration apparatus 700 comprises several components for fastening a repair graft including penetration means 420, secondary penetration means 430, tracking means 440, and insertion means 450. The penetration apparatus 700 comprises housing 710 for housing the penetration means 420, secondary penetration means 430, and insertion means 450. In a preferred embodiment, the housing 410 has a thin walled tri-limbed profile, as shown in FIGS. 26, 27 and 29. It, however, will be apparent to those skilled in the art that various modifications and variations can be made in the construction and configuration of the present invention without departing from the scope or spirit of the invention.

The housing 710 is preferably formed from an extrusion of silicone, Teflon®, or polymer having similar properties. Housing 710 comprises a plurality of passageways 711, 712, 713, 714, and 715 formed therein as shown in FIG. 29. The passageways 711, 712, 713, 714 and 715 extend along the entire length of the housing 710. Primary passageway 711 is provided for the passage of the penetration means 420. The penetration means 420 is provided to create an treatment specific hole in the wall 2 of the abdominal aorta for securing the graft thereto with a suitable fastener device. The penetration means 420 penetrates the calcified portions of the wall 2 to securely fasten the repair graft to the wall 2 in the same manner as described above in connection with the endoscopic based system. The penetration means 420 may be either a laser penetrating device or a piezoelectric penetrating device.

Secondary passageway 712 is provided for the passage of the secondary penetration means 430. The secondary penetration means 430 is also provided to create one or more openings in the vessel wall 2, in a manner similar to the primary penetration means 420, as described above.

Passageway 713 is provided within the housing 710 for passage of the insertion means 450. Passageway 714 is provided within the housing 710 for passage of the guide wire 170. Passageway 715 is provided for tracking means 440. The insertion means 450 preferably comprises a mechanism that drives an individual fastener from a fastener cartridge 470, shown in FIGS. 26 and 27, into and through the treatment specific holes created by the penetration means 420 in the repair graft and wall 2. The fastener cartridge 470 is capable of holding a procedure specific quantity of fasteners such that more than one fastener device may be sequentially displaced from the cartridge 470 to secure the repair graft to the wall 2. Fastener cartridge 470 is preferably detachably assembled to housing 710. The fastener cartridge 470 has a hollow housing 471, as shown in FIG. 26. The penetration means 420 and 430, and the placement/fastener means 450 are appropriately accommodated within the interior of the cartridge structure 460. The cartridge structure 470 and associated fastener device are complimentary with the spacer portion 820 of the housing 800 such that the penetration apparatus 700 has a flush profile, as shown in FIG. 27.

A visualization apparatus 600 for viewing the abdominal aorta to repair the aneurysm is positioned within housing 800 adjacent the minor guide wire portion 830. The visualization apparatus 600 is an intravascular ultrasound (IVUS) based system produced, for example, by Endosonics of Rancho Cordova, Calif., that comprises a housing 601 for housing radial scanning components. The housing 601 may comprise a scanning window 602, however, it is not essential for the effective operation of the visualization apparatus 600. The visualization apparatus comprises scanning catheter positioned within the housing 601 such that it scans the area of the abdominal aorta. The housing 601 is an extrusion of silicon, Teflon® or polymer or other material having similar properties. The scanning catheter extends through the minor guide wire portion 830 of housing 800. The scanning catheter creates an image of the repair that can be viewed on an external monitor, not shown.

The housing 800 also comprise transition portions 801 and 802 located on opposite ends of the penetration apparatus 700 to provide the repair apparatus 50 with a smooth profile, as shown in FIG. 27. This improves the movement of the repair apparatus 50 within the vessel 1 and adjacent arteries.

Fasteners

Reference will now be made in detail to embodiments of a fastener device, as depicted in FIGS. 30–41, 49–53 and 56–72 according to the present invention for securing the attachment device 20 to the distal end of the vessel 1. Although the fastener devices are described in connection with the repair of an aneurysm in a vessel, the use of the fastener devices in other surgical procedures as a replacement for sutures is contemplated to be within the scope of the present invention. The fastener devices described herein may be used to secure a first component to a second component. The first component includes but is not limited to surgical components (e.g., a graft) and tissue. The second component includes but is not limited to surgical components, vessels and tissues.

Figure 30:
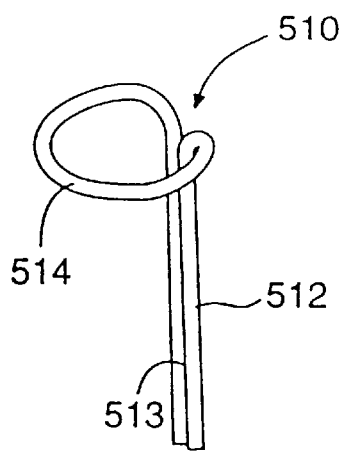
FIGS. 30 and 31 are perspective views of a wire fastener for securing the cuff detail of a surgical cuff to a vessel wall according to an embodiment of the present invention.
Figure 31:
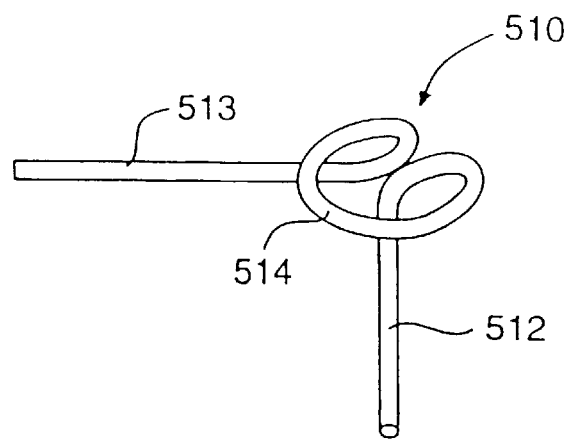

FIGS. 30 and 31 depict a fastener 510 according to an embodiment of the present invention. The fastener 510 comprises a pair of normally splayed fastening legs 512 and 513. The fastener 510 also comprises an anchoring portion 514, as shown in FIG. 31. The fastener 510 is preferably formed from a wire-like material. The anchoring portion 514 may be formed from a coil of the wire-like material. The legs 512 and 513 are temporarily reoriented, as shown in FIG. 30, for storage on a fastener cartridge 460 and for enabling the attachment of the attachment device 20 to the wall 2. As the legs 512 and 513 are inserted through the attachment device 20 and the wall 2, the legs 512 and 513 return to a normal, as manufactured, splayed position, as shown in FIG. 31. When the fastener 510 is in a fastened position within the vessel, the anchoring portion 514 is positioned on one side of the attachment device 20 and wall 2 (intima/graft) adjacent the attachment device 20. The splayed legs 512 and 513 are positioned on the opposite side of the attachment device 20 and wall 2 (adventia) adjacent the wall 2. The anchoring portion 514 and splayed legs 512 and 513 apply compressive forces to the wall 2 and the attachment device 20 to securely fastening the attachment device 20 to the vessel 1.

The fastener 510 is preferably formed from a stainless steel, such that the legs 512 and 513 return to the splayed position to secure the attachment device 20 to the wall 2. It, however, will be apparent to those skilled in the art that various modifications and variations can be made in the construction and configuration of the present invention without departing from the scope or spirit of the invention. For example, the fastener 510 may be formed from other suitable materials including but not limited to superelastic titanium, or other procedure/performance appropriate materials such as plastics having similar properties including, but not limited to biocompatability, elasticity, and flexural strength. Thus, it is intended that the present invention cover the modifications and variations of the invention, provided they fall within the scope of the appended claims and their equivalents.

Figure 32:
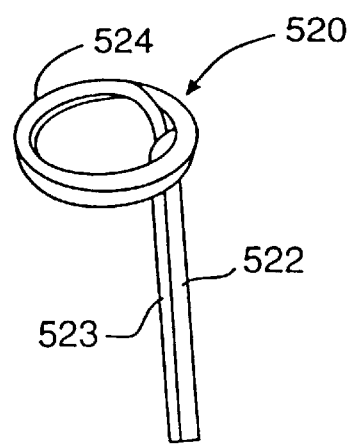
FIGS. 32 and 33 are perspective views of a wire fastener according to another embodiment of the present invention for securing the cuff detail of a surgical cuff to a vessel wall.
Figure 33:
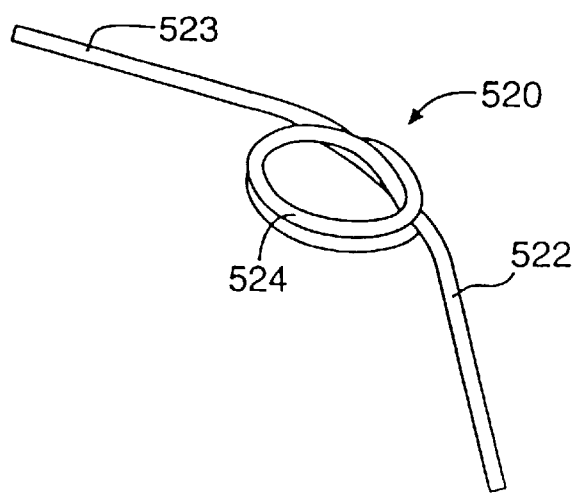

FIGS. 32 and 33 depict a fastener 520 according to another embodiment of the present invention. The fastener 520 comprises a pair of normally splayed fastening legs 522 and 523. The fastener 520 also comprises an anchoring portion 524. The fastener 520 is also preferably formed from a wire-like material. The anchoring portion 524 may be formed from at least one coil of the wire-like material (i.e., a wound portion). The legs 522 and 523 are temporarily compressed, as shown in FIG. 32, for storage in a fastener cartridge 460 and for facilitating the attachment of the attachment device 20 to the wall 2. Similar to the embodiment described above in connection with FIGS. 30 and 31, as the legs 522 and 523 are inserted through the attachment device 20 and the wall 2, the legs 522 and 523 return to a normally splayed position, as shown in FIG. 32. When the fastener 520 is in a fastened position within the vessel, the anchoring portion 524 is positioned on one side of the attachment device 20 and wall 2 adjacent the attachment device 20. The splayed legs 522 and 523 are positioned on another side of the attachment device 20 and wall 2 adjacent the wall 2. The anchoring portion 524 and splayed legs 522 and 523 apply compressive forces to the wall 2 and the attachment device 20 to securely fastening the attachment device 20 to the vessel 1.

Figure 34:
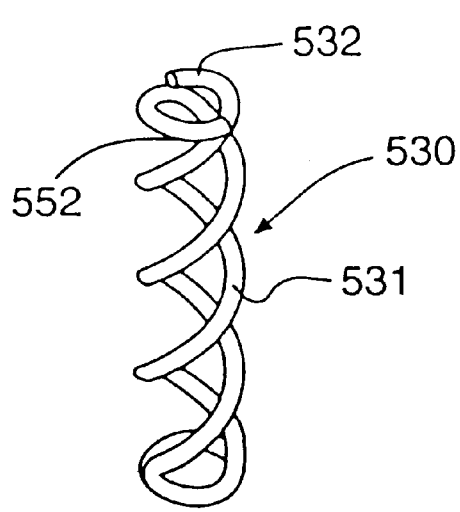
FIGS. 34 and 35 are perspective views of a wire fastener according to another embodiment of the present invention for securing the cuff detail of a surgical cuff to a vessel wall.
Figure 35:
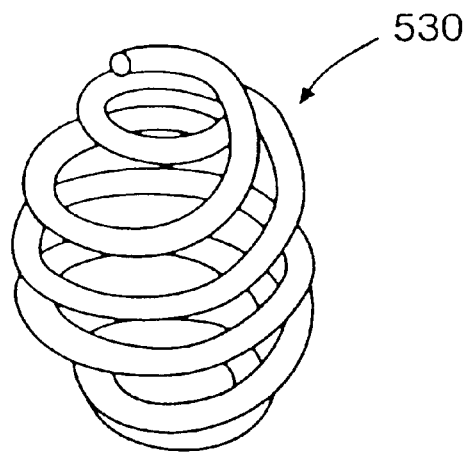
Figure 42:
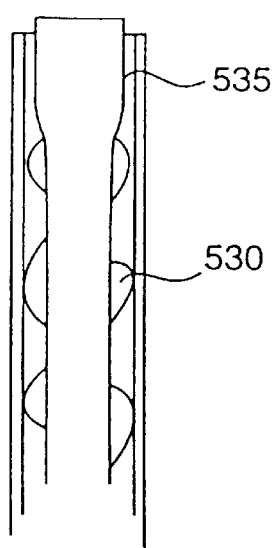
FIG. 42 is a schematic view of an embodiment of the penetration device according to the present invention having fasteners, as shown in FIGS. 34, 37, 38 and 39 stored thereon.
Figure 43:
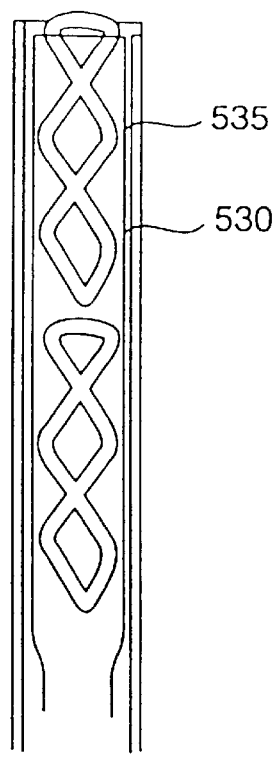
FIG. 43 is a schematic view of an another embodiment of the penetration device according to the present invention having fasteners, as shown in FIGS. 36, 37, 38 and 39 stored therein.
Figure 44:
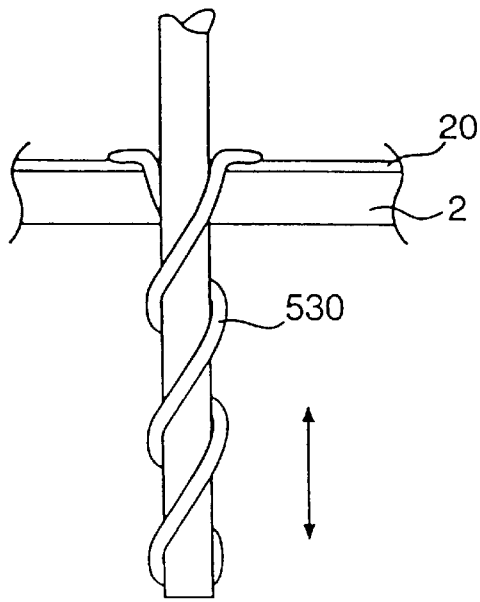
FIGS. 44 and 45 are perspective views illustrating the fastener attachment of the cuff detail to the vessel wall using a fastener as shown in FIGS. 34 and 35 according to an embodiment of the present invention.
Figure 45:
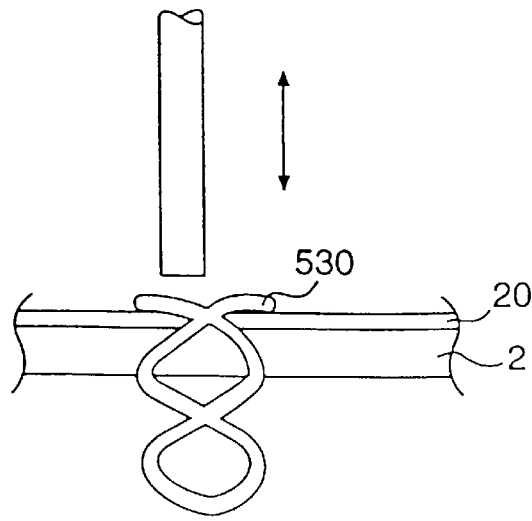
Figure 46:
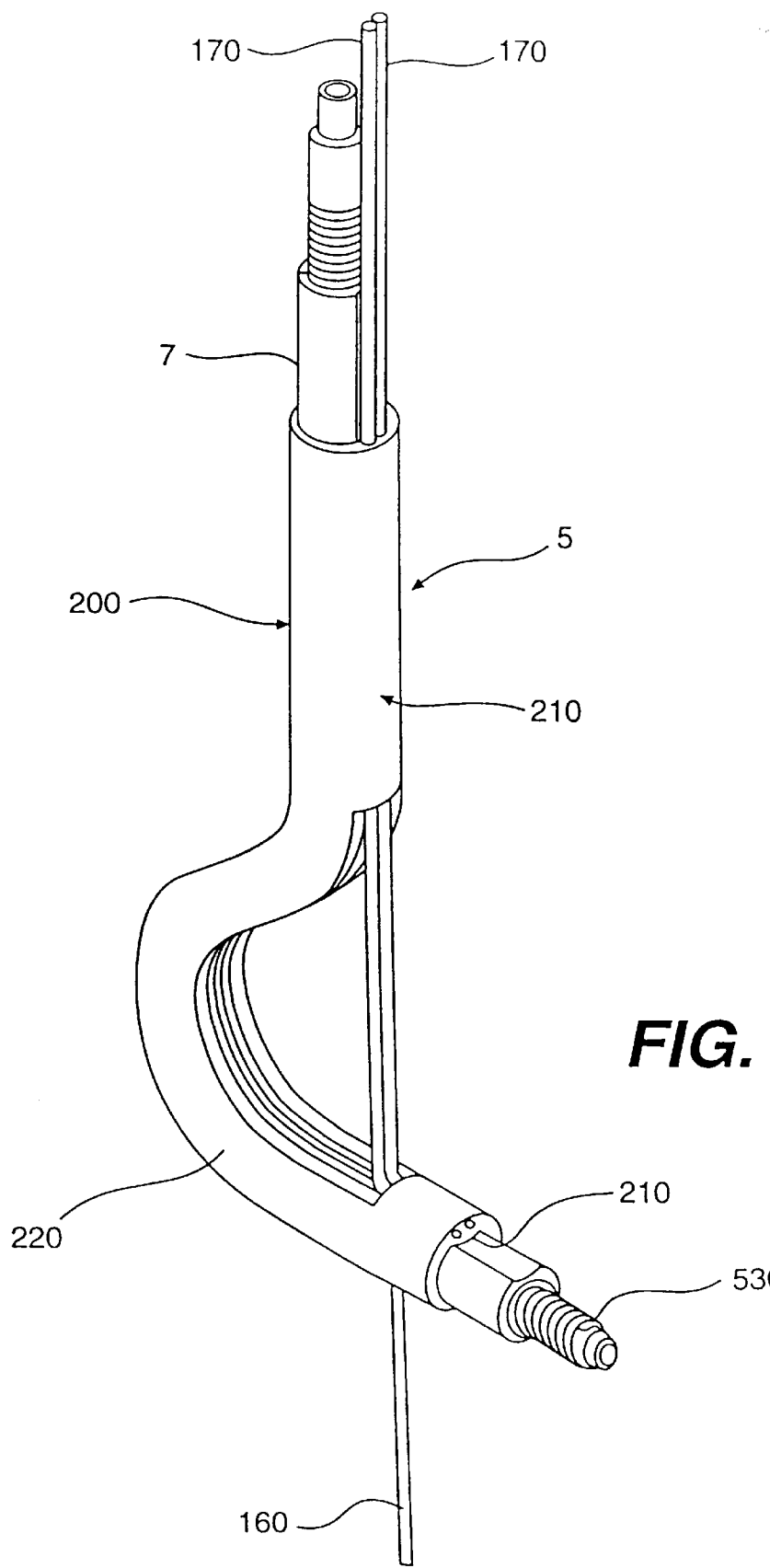
FIG. 46 is a perspective view of another embodiment of an IntraVascular Angiography (IVA) based repair system according to an another embodiment of the present invention.

FIGS. 34 and 35 depict a fastener 530 according to another embodiment of the present invention. Fastener 530 is a spring type fastener, which may comprise a coil spring. The fastener 530 is also formed from a wire-like material. The fastener 530 comprises a plurality of coils, as shown in FIG. 34. The end portions 531 and 532 of the wire-like material are preferably located on the same end of the fastener 530, as shown in FIGS. 29, 30, and 34–36. Unlike fastener 510 and 520, the fastener 530 is temporarily elongated for storage in the fastener cartridge 535, as shown in FIGS. 42, 43, and 46. As the fastener 530 is inserted through the attachment device 20 and wall 2 using the insertion means 450 on the penetration device 7, as shown in FIG. 44, the fastener 530 remains in an elongated position until the insertion means 450 is removed from the treatment specific hole 3 created in the wall 2 of the vessel, and the attachment device 20 formed by the penetration apparatus 7. The fastener 530 then assumes a collapsed position, as shown in FIG. 35. When the fastener 530 is in a fastened position within the vessel 1, the end portions 531 and 532 are positioned on one side of the attachment device 20 and wall 2 adjacent the attachment device 20, as shown in FIG. 45. The remaining portion of the fastener 530 is positioned on another side of the attachment device 20 and wall 2 adjacent the wall 2. The fastener 530 apply compressive forces to the wall 2 and the attachment device 20 to securely fastening the attachment device 20 to the vessel 1. Fastener 530 may be formed from stainless steel; a superelastic alloy, for example titanium; or any other procedure/performance-appropriate materials.

Figure 36:
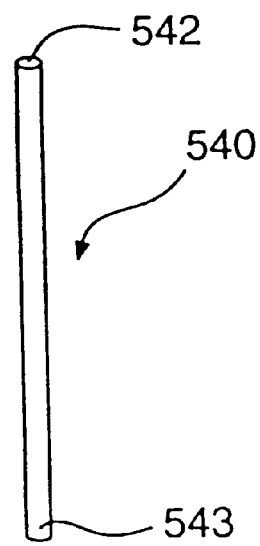
FIGS. 36, 37, 38, 39, 40 and 41 are perspective views of a fastener according to another embodiment of the present invention for securing the cuff to a vessel wall.
Figure 37:
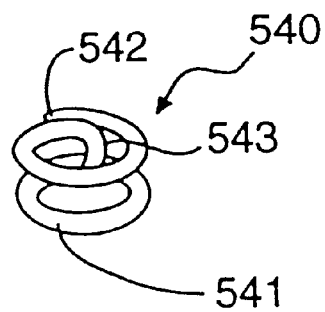
Figure 38:
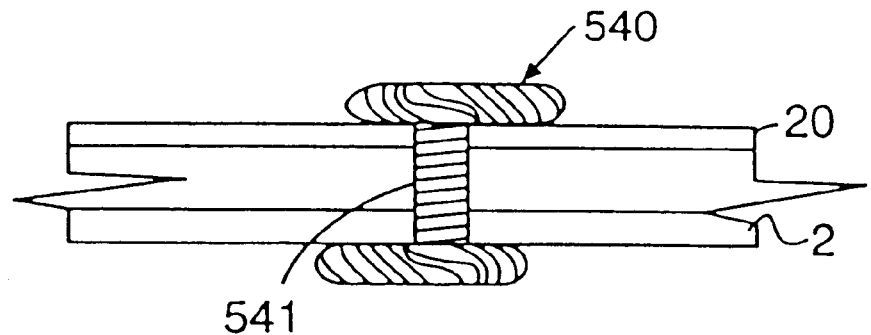
Figure 39:
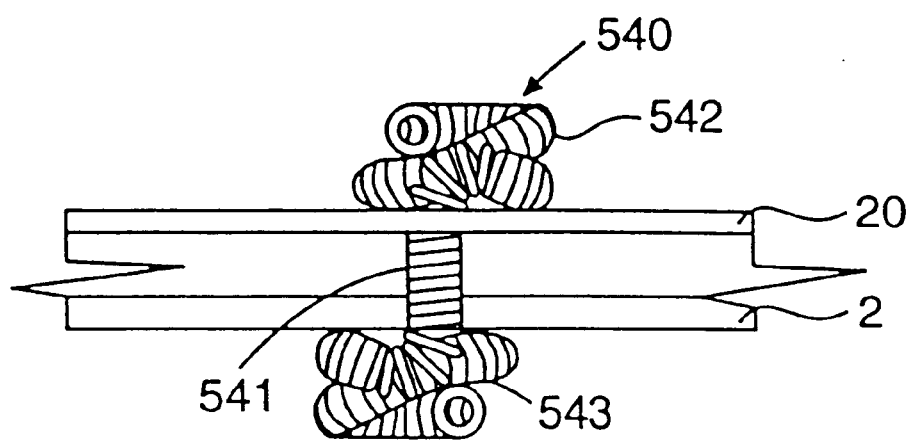
Figure 40:
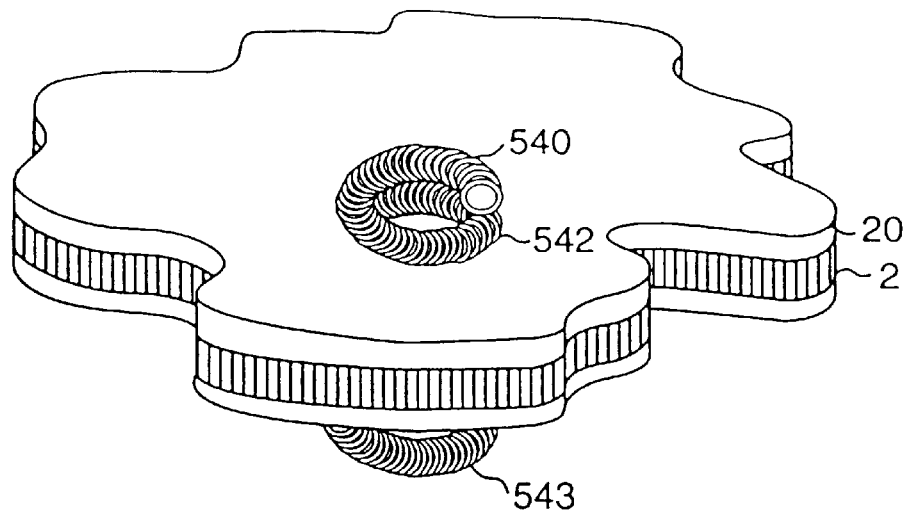
Figure 41:
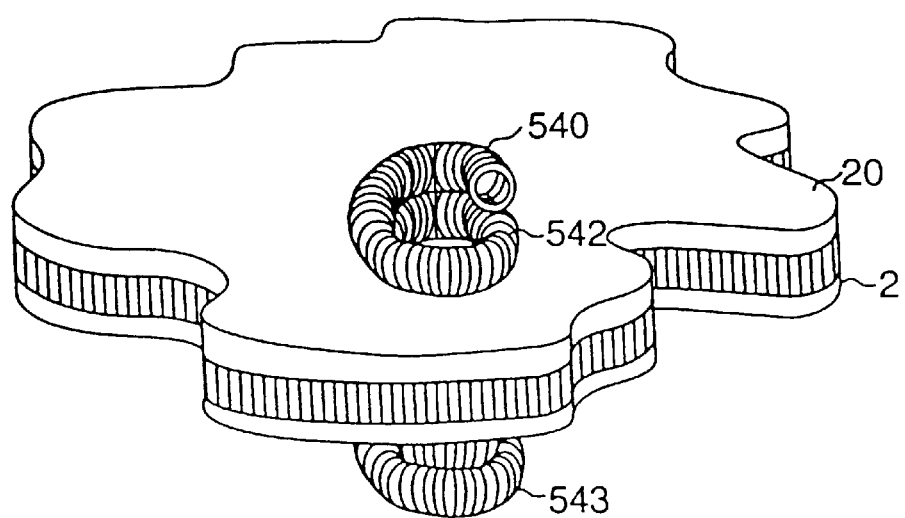

FIGS. 36, 37, 38, and 39 depict a fastener 540 according to another embodiment ofthe present invention. Fastener 540 is a coil spring type fastener. Fastener 540 comprises a mid-section 541, and semi-knotted end portions 542 and 543. The fastener 540 is also formed from a coil spring using materials, as described above. Preferably the fastener 540 is formed from stainless steel or a superelastic alloy, for example titanium. The fastener 540 is substantially linear, as shown in FIG. 36, when stored in a fastener cartridge, not shown. As the fastener 540 is inserted through the attachment device 20 and wall 2, the fastener 540 returns to its normally coiled configuration, as shown in FIG. 37. The fastener 540 applies compressive forces to the wall 2 and the attachment device 20 to securely fastening the attachment device 20 to the vessel 1 such that one semi-knotted overlapping end portion 542 is positioned adjacent the attachment device 20 and the other semiknotted end portion 543 is positioned adjacent the wall 2 of the vessel 1, as shown in FIGS. 38 and 39. FIG. 28 depicts an axially wound fastener 540. FIG. 40 depicts the fastener 540 of FIG. 38 secured to the wall 2. FIG. 39 depicts a radially wound fastener 540. FIG. 41 depicts the fastener 540 of FIG. 39 secured to the wall 2. The fastener 540 is termed a coiled coil spring type fastener. The coil spring which makes up the fastener is itself coiled during manufacture to assume the coiled configuration shown in FIGS. 38–40. Fastener 540 is inserted through the attachment device 20 and the wall 2 using an insertion means in manner described above for fastener 530.

Figure 49:
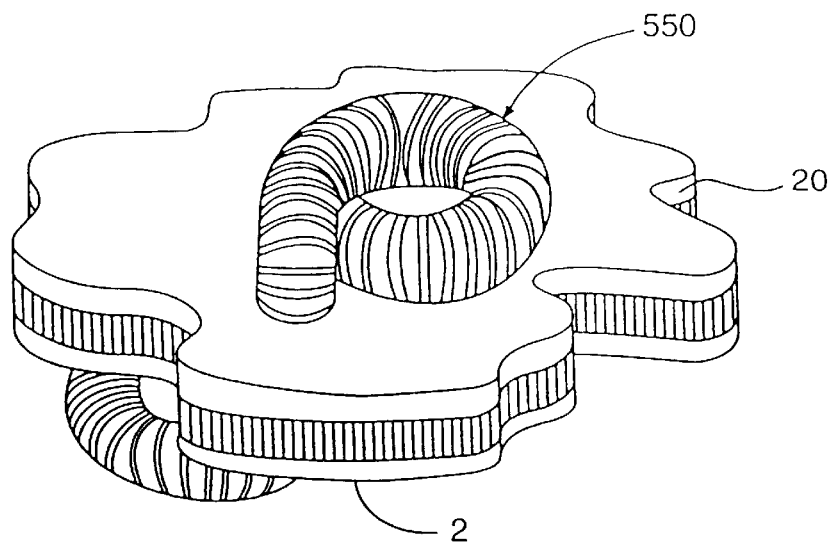
FIGS. 49, 50, and 51 are perspective views of a fastener according to another embodiment of the present invention.
Figure 50:
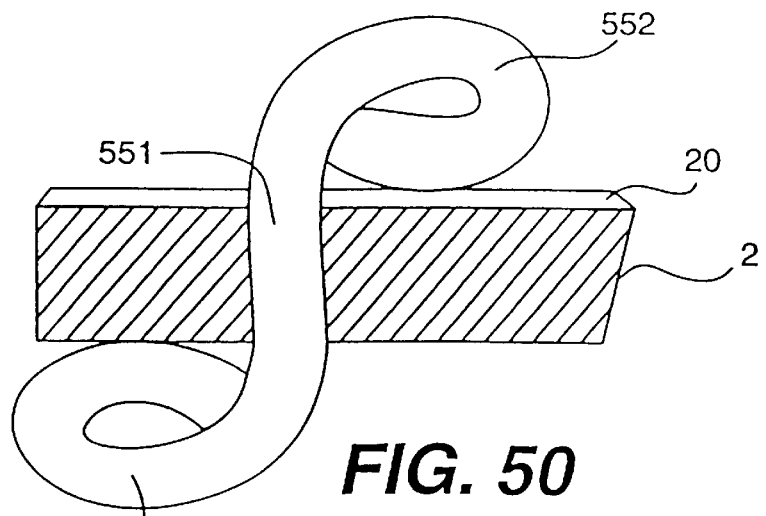
Figure 51:
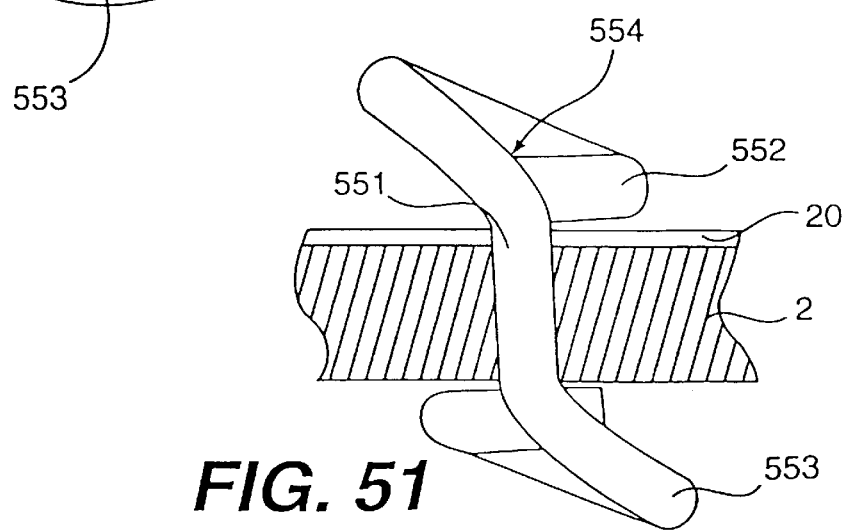

FIGS. 49, 50, and 51 depict a fastener 550 according to another embodiment of the present invention. Fastener 550 is a coil spring type fastener formed from stainless steel, or a superelastic alloy, for example titanium, or any other procedure/performance appropriate materials. Fastener 550 is substantially linear, as shown in FIG. 36, when temporarily stored in a fastener cartridge, not shown.

The fastener 550 is a coiled coil spring type fastener which is coiled into its fastening shape during manufacture. Fastener 550 may comprise a plurality of coiled coil springs connected together. The embodiment shown in FIG. 49 comprises two entwined springs. The coil diameter and wire gauge for the depicted design are approximately 0.04 inches and 0.005 inches respectively. It, however, is contemplated that the present invention is not limited to these dimensions. Outside coil diameters greater than 0.04 inches and less than 0.04 inches (such as, for example, 0.03 inches) are considered to be well within the scope of the present invention. The fastening force of the fastener 550 can be adjusted to suit a particular purpose by varying the coil diameter, wire gauge, number of coils, and number of coil springs. The fastener 550 is termed a coiled coil spring due to the fact that the coil spring is further coiled into a shape suitable for fastening during manufacture. The coiled coil springs that comprise the fastener 550 are spot welded together at least one point along their lengths. Any suitable connection means that serves to keep the springs of the coiled coil in a fixed relationship with one another is within the scope of the present invention, and may be used in lieu of spot welding.

Fastener 550 comprises a midsection 551, and under lapping end portions 552 and 553. Prior to insertion the fastener 550 is temporarily straightened and placed about an insertion means. The fastener 550 is inserted through the attachment device 20 and the wall 2 using a process similar to that described above for fastener 530. Following insertion the core is removed and the fastener 550 returns to its normally coiled configuration, as shown in FIGS. 49–51. The manufactured configuration of the fastener 550 provides the innovative method for securing the attachment device. The end portions 552 and 553 underlap at point 554 providing a locking mechanism for the fastener 550. The under lapping design of the fastener 550 prevents the attachment device 20 and the wall 2 from being pulled apart.

Figure 52:
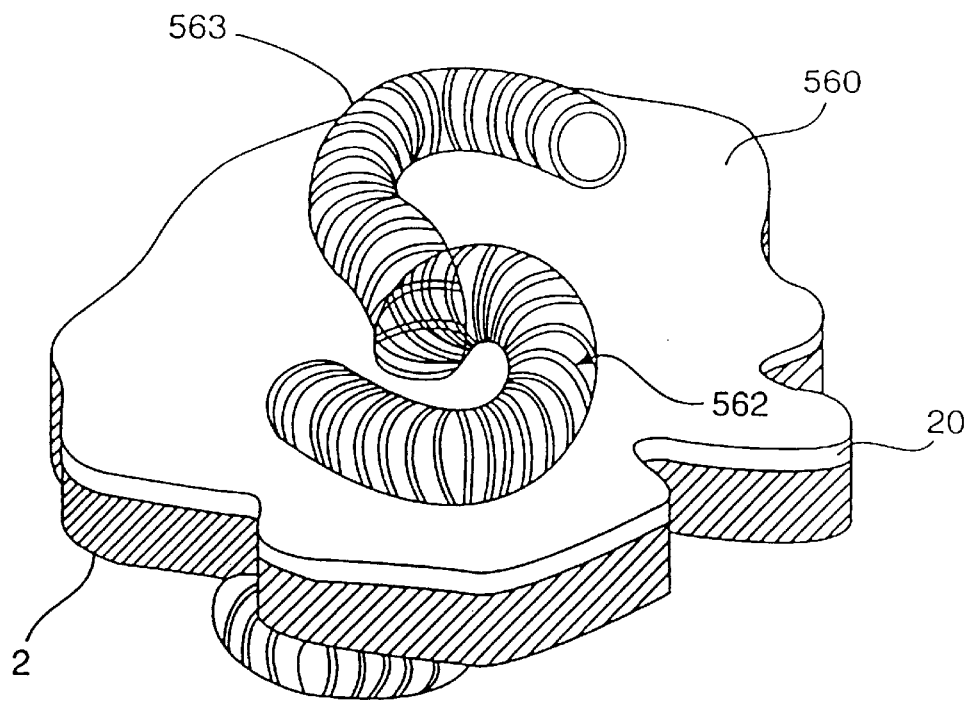
FIGS. 52 and 53 are perspective views of a fastener according to another embodiment of the present invention for securing the cuff to a vessel wall.
Figure 53:
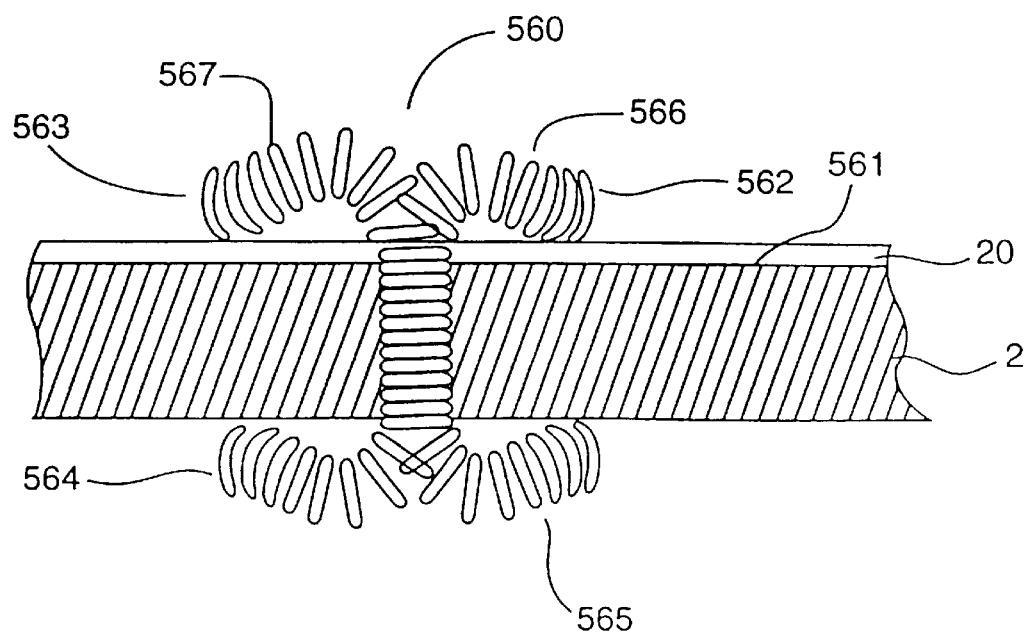

FIGS. 52 and 53 depict a fastener 560 according to another embodiment of the present invention. Fastener 560 is a coiled coil spring type fastener formed from stainless steel, or a superelastic alloy, for example titanium, or any other procedure/performance appropriate materials. Similar to fastener 550, fastener 560 also utilizes coiled coil springs. Fastener 560 comprises a plurality of springs entwined together. The fastener 560 may be a single coiled coil spring or a plurality of coiled coil springs entwined together such as in fastener 550 described above. The preferred embodiment, as shown in FIGS. 52 and 53, comprises two coiled coil springs 562 and 563. However, it is within the scope of the present invention that the fastener 560 may comprise more or less than two springs. The coil diameter and the wire gauge for the depicted design is approximately 0.04 inches and 0.005 inches respectively. The fastening force of the fastener 560 can be adjusted to suit a particular purpose by varying the coil diameter, wire gauge, number of coils, and the number of springs.

Fastener 560 comprises a midsection 561, and end portions 562, 563, 564 and 565. Prior to insertion the fastener 560 is temporarily straightened and placed about an insertion means. The fastener 560 is inserted through the attachment device 20 and the wall 2. Following insertion, the insertion means is removed and fastener 560 unravels allowing the coiled coil springs 562 and 563 to return to their manufactured configuration, as shown in FIGS. 52 and 53. The springs 562 and 563 may be spot welded together at least one point along the midlength 561. The ends 564, 565, 566 and 567 of the springs are not welded together allowing them to separate when the insertion means is removed. Any suitable connection means that serves to keep the springs of the fastener 560 in a fixed relationship with one another is within the scope of the present invention, and may be used in lieu of spot welding.

Both fasteners 550 and 560, described above, use coiled coil springs with elastic/mechanical memories. Following insertion through the attachment device 20 and the wall 2, the coiled coil springs remember their manufactured form, and return to that form securing the attachment device 20 to the wall 2.

Figure 56:
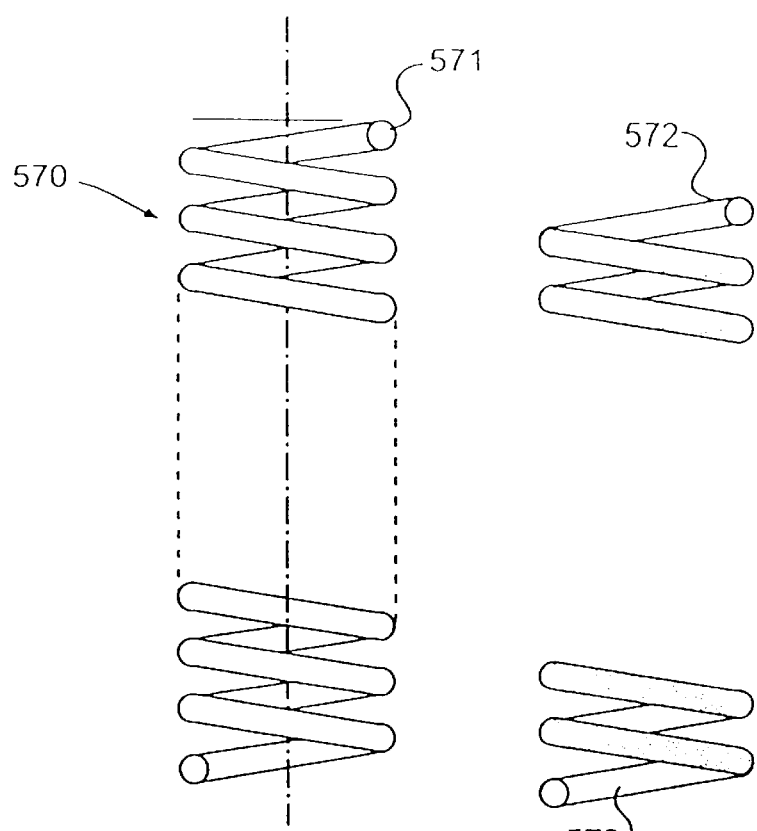
FIGS. 56, 57 and 58 are perspective views of a fastener according to another embodiment of the present invention.
Figure 57:
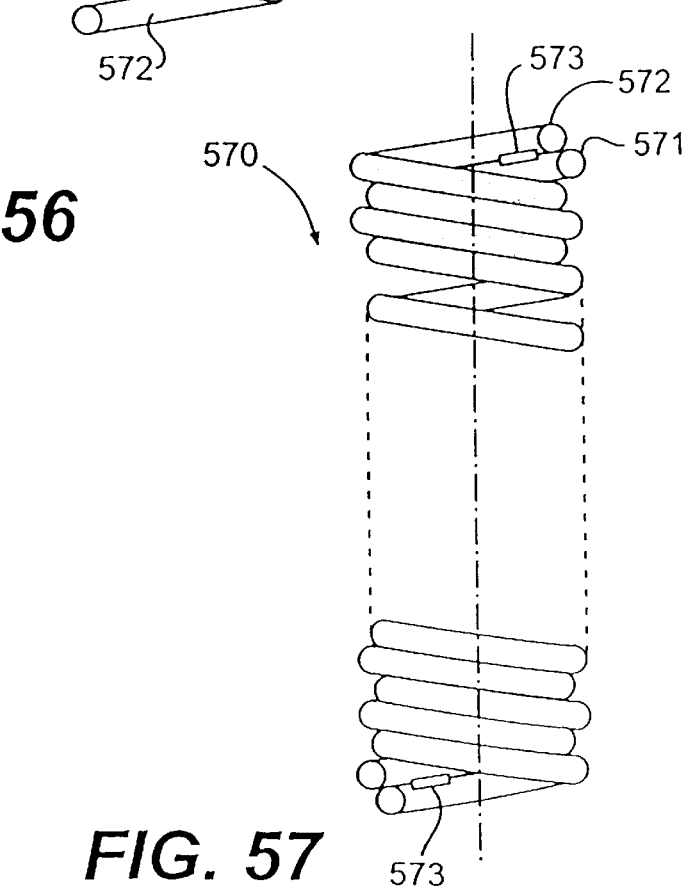
Figure 58:
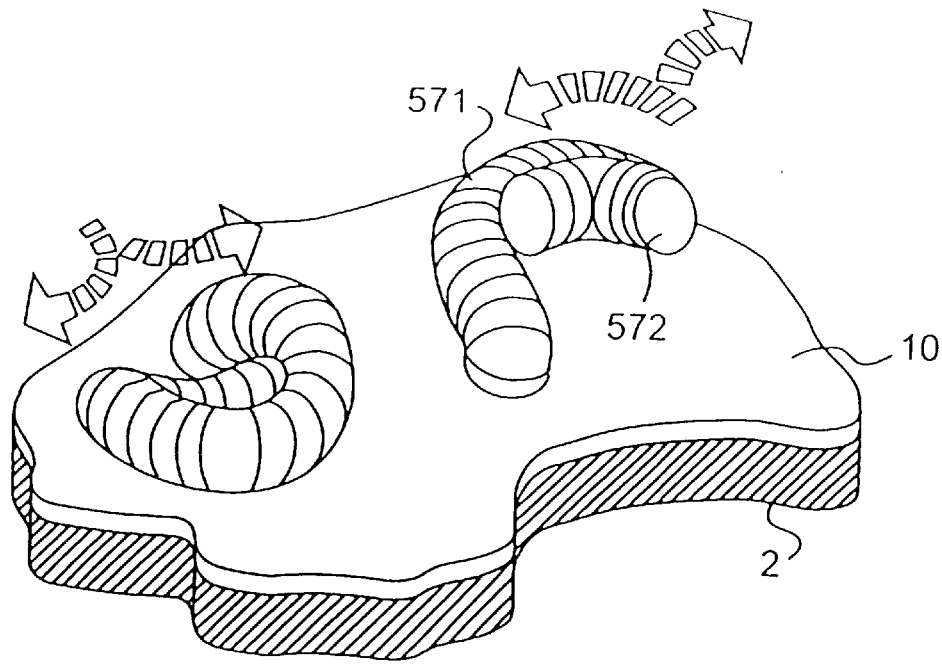

The holding potential of the coiled-coil fastener 570 may be further enhanced according to the embodiment of FIGS. 56–58. The fastener 570 includes a central coiled fastener 571. The fastener 570 further includes at least one short coiled insert 572. The coiled insert 572 is located adjacent the end portion of fastener 571, as shown in FIGS. 56 and 57. The short coiled insert 572 may be entwined with the fastener 571 at its ends to create unique head features. When the core over which the fastener 570 is temporarily positioned is removed the fastener 570 returns to its as-manufactured configuration. In this position, the at least one coiled insert 572 separates from the fastener 571 host creating a dimensional disturbance and additional resistance to fastener withdrawal. The at least one short coiled insert 572 is spot welded as shown at 573 to prevent complete separation from the fastener 571.

It is contemplated that the above-described coil spring fasteners may be formed either axially or radially wound coil springs. Furthermore, it is contemplated that coil spring may have a circular, rectangular, triangular or other cross sectional configuration. It is also contemplated that the above-described fasteners may be surface treated to increase friction between the fastener and the surrounding tissue. Furthermore, it is contemplated that a polymeric material may be used rather than metal. In addition to varying coil diameter, wire gauge, number of coils and number of interwound springs to modify the holding force of the coiled-coil fastener, changing the spring's pitch between coils will also enhance the fastener's performance.

The fasteners according to the present invention are advanced to the surgical site either over or within the penetration assembly 7, as discussed above by activation of an advancing mechanism positioned remotely with respect to the patient. To minimize the complexity of the mechanism it is necessary to tightly control the over-mandrel length of the fastener. Compression of the fastener is inherent to its design as it transitions from its "as-manufactured" form to its "insertion-ready" form and will create significant functional problems unless anticipated in the fastener/fastener advance mechanism design. The inventors of the fasteners of the present invention have been able to remove fastener compression from the fastener advancement equation. According to one embodiment, the fastener can be dimensioned in such a way that the "slack" which is created within the fastener as it transitions from its "as-manufactured" to its "insertion-ready form," is taken up as it is wound over the insertion assembly 450. The inside diameter of the coil spring is the same as or slightly smaller than the insertion assembly 450 over which or within which it is temporarily positioned. This "dimensioning" facilitates both the pre-compression of the fastener on or within the penetration assembly 7 and its uniform advancement to the surgical site.

According to another embodiment, the fastener may be insert molded within a gelatin or similar dissolvable medium while in its "insertion-ready" form. The resultant "tube-like" component is non-compressible and facilitates both the fastener's easy loading over or within the penetration means and thereafter its uniform advancement to the surgical site where ultimately it spans the graft/adventitia matrix. The blood present dissolves the gelatin coating about and within the interstices of the fastener enabling resumption of its "as-manufactured" form and the compressive attachment of graft to vessel wall.

Figure 59:
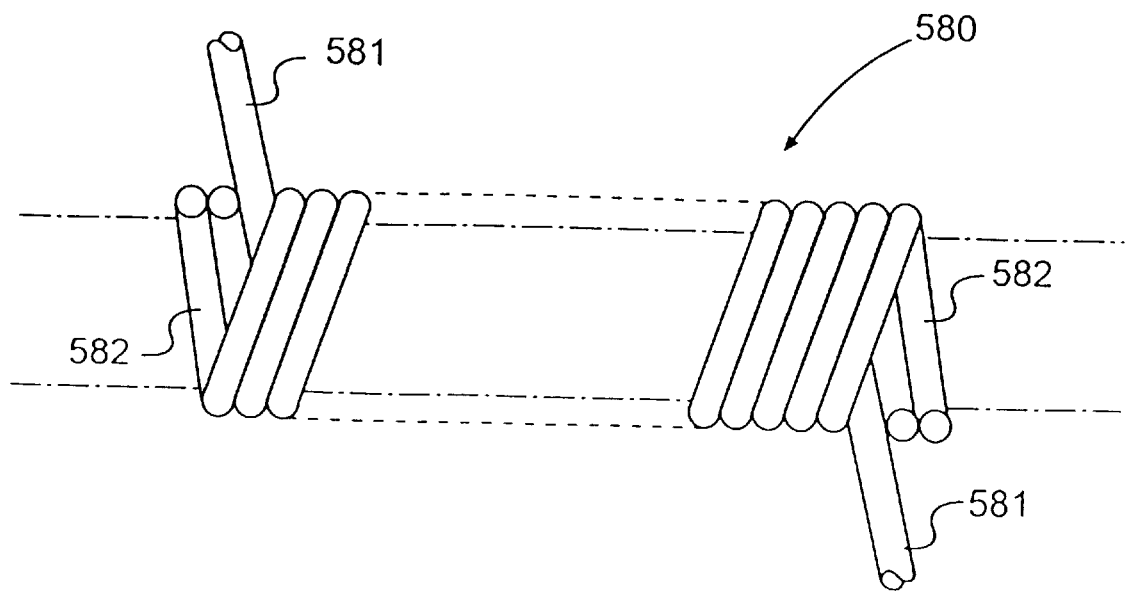
FIG. 59 is a perspective view of a fastener according to another embodiment of the present invention.

According to another embodiment, the fasteners may incorporate a dissolvable suture material. As shown in FIG. 59, the fastener 580 incorporates a dissolvable suture 581 wound between the individual coils 582 of the fastener 580. The provision of the dissolvable suture 581 prevents longitudinal compression the fastener 580 on the insertion assembly, described above. Furthermore, the use of the suture permits uniform advancement of the fastener 580 along the insertion assembly and penetration assembly during the surgical procedure. It is contemplated that the use of the dissolvable suture 581 is not limited to fastener 580. Rather, the use of the dissolvable suture 581 with any fastener having at least a coiled spring portion, including but not limited to the above-described embodiments, is considered to be well within the scope of the present invention.

FIGS. 60–72 depict various embodiments of a preferred fastener that is thermoelectrically inserted in place into the first and second components during a surgical procedure. The fasteners of FIGS. 60–72 include a partially insulated filament, which when heated burns through the first component and at least a portion of the second component as pressure is applied to the fastener by a placement device. The fastener when inserted, secures the first and second components to one another.

An energy source, located for example within an insertion assembly supplies the necessary energy to the heat transmitting source. The energy source comprises an electrical assembly that applies a current to the fastener such that the partially insulated component of the fastener is heated. The insertion means applies pressure to the fastener such that it is inserted through a burn incision created by the exposed heated filament. The incision created by the exposed heated filament is sized to permit insertion of the fastener only and to prevent collateral damage of surrounding tissue. It is contemplated by the present inventions that the fastener may be used to secure a surgical component to a vessel wall or to tissue. It is further contemplated that the fastener in accordance with the present invention may be used to secure one tissue to another.

Figure 60:
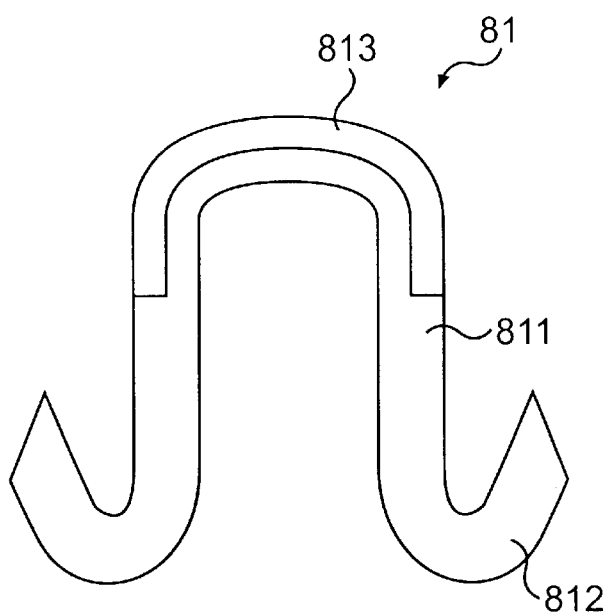
FIG. 60 is a schematic view of a fastener according to another embodiment of the present invention.
Figure 61:
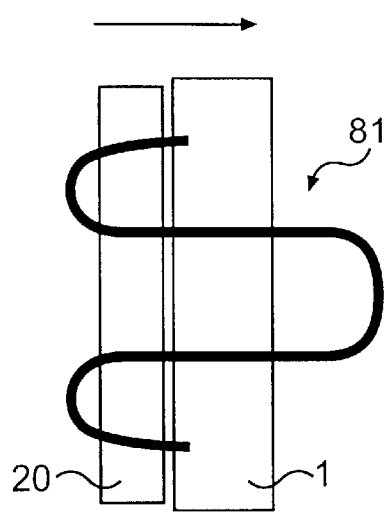
FIG. 61 is a schematic view of the fastener FIG. 60 in an inserted position.

Specific embodiments of the preferred electrically activated, thermally inserted fastener will now be described. FIG. 60 illustrates an endostaple fastener 81 in accordance with an embodiment of the present invention. Fastener 81 includes a midsection 811 and a pair of free end portions 812. The fastener is preferably formed from an insulated filament. The free end portions 812 are preferably configured to permit their penetration of the surgical component, tissue and/or vessel wall, as illustrated in FIG. 61. The midsection 811 of the fastener 81 includes a heat penetration area 813. The heat penetration area 813 preferably includes a partially insulated filament component, however, other heat transmitting sources are contemplated. The heat penetration area 813 is heated when an energy source is applied to it and subsequently permits insertion of the fastener 81 in the direction indicated by the arrow in FIG. 61 through the surgical component 20 and the vessel 1 by burning an incision in the first component and at least a portion of the second component. The configuration of the end portions 812 and the force applied by the insertion means permits the free end portions 812 to penetrate at least the component 20 and preferably a portion of the vessel 1 to further anchor the fastener 81 and secure the component 20 to the vessel 1. The fastener 81 would be used in a similar manner to secure a first tissue to a second tissue.

Figure 62:
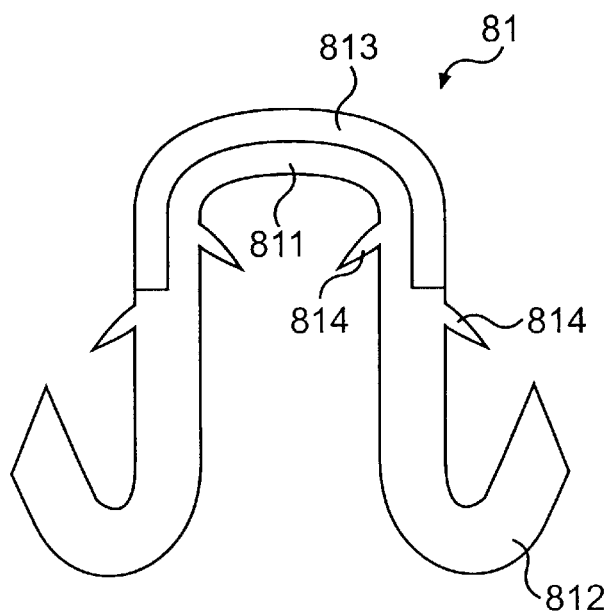
FIG. 62 is a schematic view of a fastener according to another embodiment of the present invention.
Figure 63:
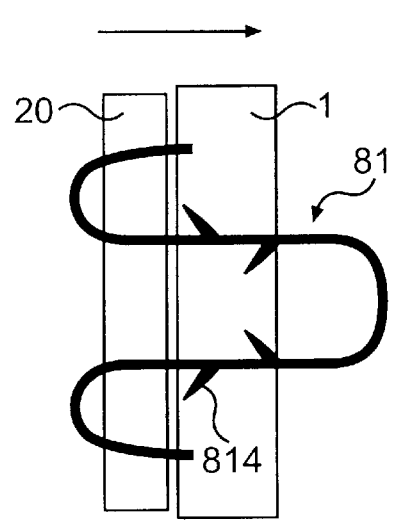
FIG. 63 is a schematic view of the fastener of FIG. 62 in an inserted position.

FIGS. 62 and 63 illustrate a variation of the fastener 81. The midsection 811 of the fastener 81 includes at least one burr or hooking assembly 814. The at least one hooking assembly 814 extends from the midsection 811 such that when the fastener 81 is inserted into the component 20 and vessel 1, the hooking assembly 814 provides a means for preventing the removal of the fastener 81. The at least one hooking assembly 814 engages at least one of the first component and the second component to prevent removal of the fastener 81 upon insertion.

Figure 64:
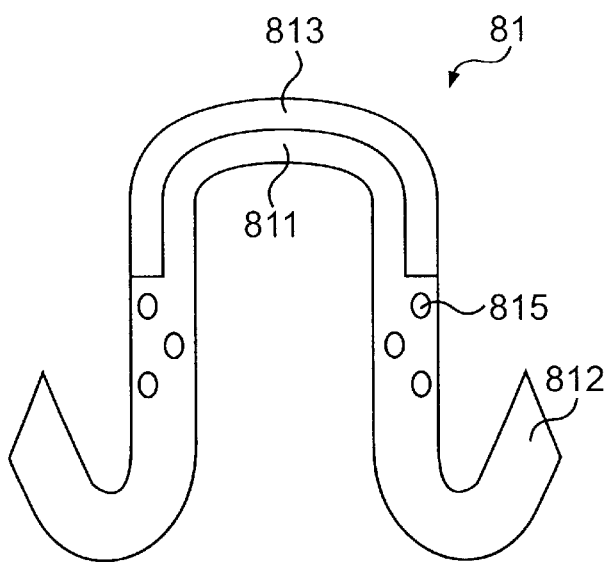
FIG. 64 is a schematic view of a fastener according to another embodiment of the present invention.
Figure 65:
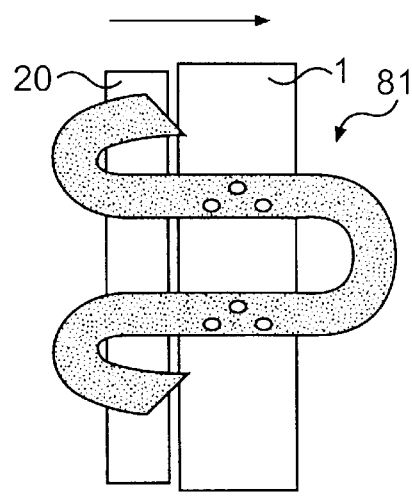
FIG. 65 is a schematic view of the fastener of FIG. 64 in an inserted position.

FIGS. 64 and 65 illustrate another variation of the fastener 81. The midsection 811 includes at least one opening 815 formed therein. The at least one opening 815 allows tissue ingrowth such that the vessel 1 or tissue will grow through the at least one opening 815 to further secure the fastener 81 and prevent removal of the fastener 81 from the component 20 and vessel 1, as shown in FIG. 65. It is contemplated that the at least one opening 815 may be filled with a polymeric or metallic gauze that swells after insertion into the vessel 1 or tissue. Tissue in growth may then occur through the gauze. Tissue in growth will provide exceptional protection against removal of the fastener.

Figure 66:
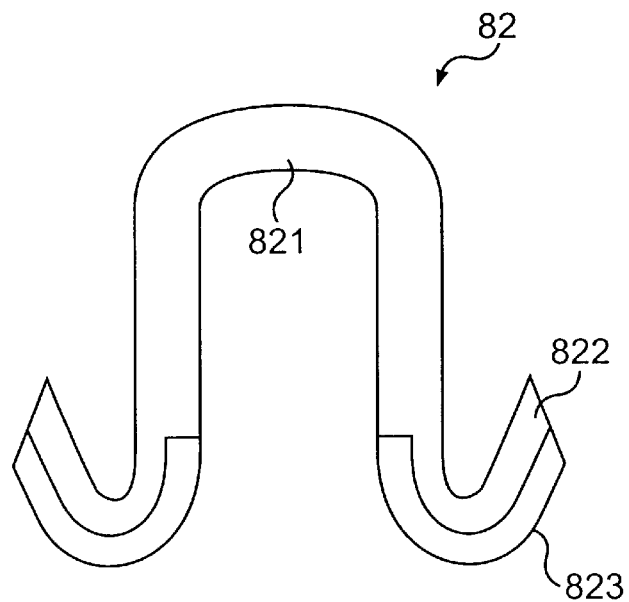
FIG. 66 is a schematic view of a fastener according to another embodiment of the present invention.
Figure 67:
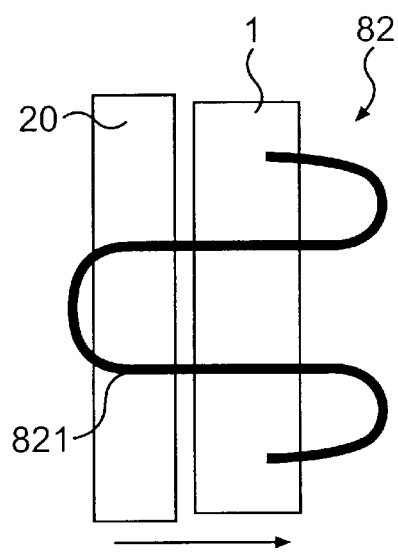
FIG. 67 is a schematic view of the fastener of FIG. 66 in an inserted position.

FIGS. 66 and 67 illustrate another embodiment of the endostaple fastener according to the present invention. The fastener 82 includes a midsection 821 and a pair of free end portions 822. The midsection 821 and free end portions 822 have a similar construction to the midsection 811 and free end portions 812 of fastener 81 with the exception of the location of the non-insulated filament. In the embodiment of FIGS. 66 and 67, each of the free end portions 822 include a heat penetration area 823, which permits insertion of the fastener 82 in the direction indicated by the arrow in FIG. 67 through the component 20 and the vessel 1. It is contemplated that the fastener 82 may be used to secure tissue to tissue. The free portions further engage the vessel 1 and/or tissue to secure the fastener 82 in place.

FIGS. 68 and 69 illustrate a variation of the fastener 82. The midsection 821 includes a bent portion 8210 that when in an inserted position lies flat against the first component which enhances the fixation forces applied on the first component and the second component.

FIGS. 70 and 71 illustrate another variation of fastener 82. The midsection 821 of the fastener 82 includes at least one burr or hooking assembly 824. The at least one hooking assembly 824 extends from the midsection 821 such that when the fastener 82 is inserted into the component 20 and vessel 1 using a suitable insertion means, the hooking assembly 824 provides a means for preventing the removal of the fastener 82 by engaging the vessel 1 or tissue, as shown in FIG. 71.

It is contemplated that any of the above-described variations may be combined together. For example, the at least one opening may be used in connection with the at least one hooking assembly.

The fasteners 81 and 82 are formed preferably formed from an inconel wire having a silver plated coating. The silver plate coating acts as an insulating layer. It, however, is contemplated that other suitable materials having similar physical properties may be used in the present invention. The fastener may have a flat cross section. Alternatively, the fastener may have a round cross section. The heat transmitting section of the fastener is preferably formed from an exposed portion of the inconel wire. Other heat generating sources are considered to be well within the scope of the present invention. It is contemplated that any of the above-described embodiments illustrated in FIGS. 60–71 may be stored prior to insertion on a tape such that a plurality of fasteners may be positioned within the insertion assembly such that multiple fasteners can be inserted during a surgical procedure without removal of the insertion assembly.

Figure 72:
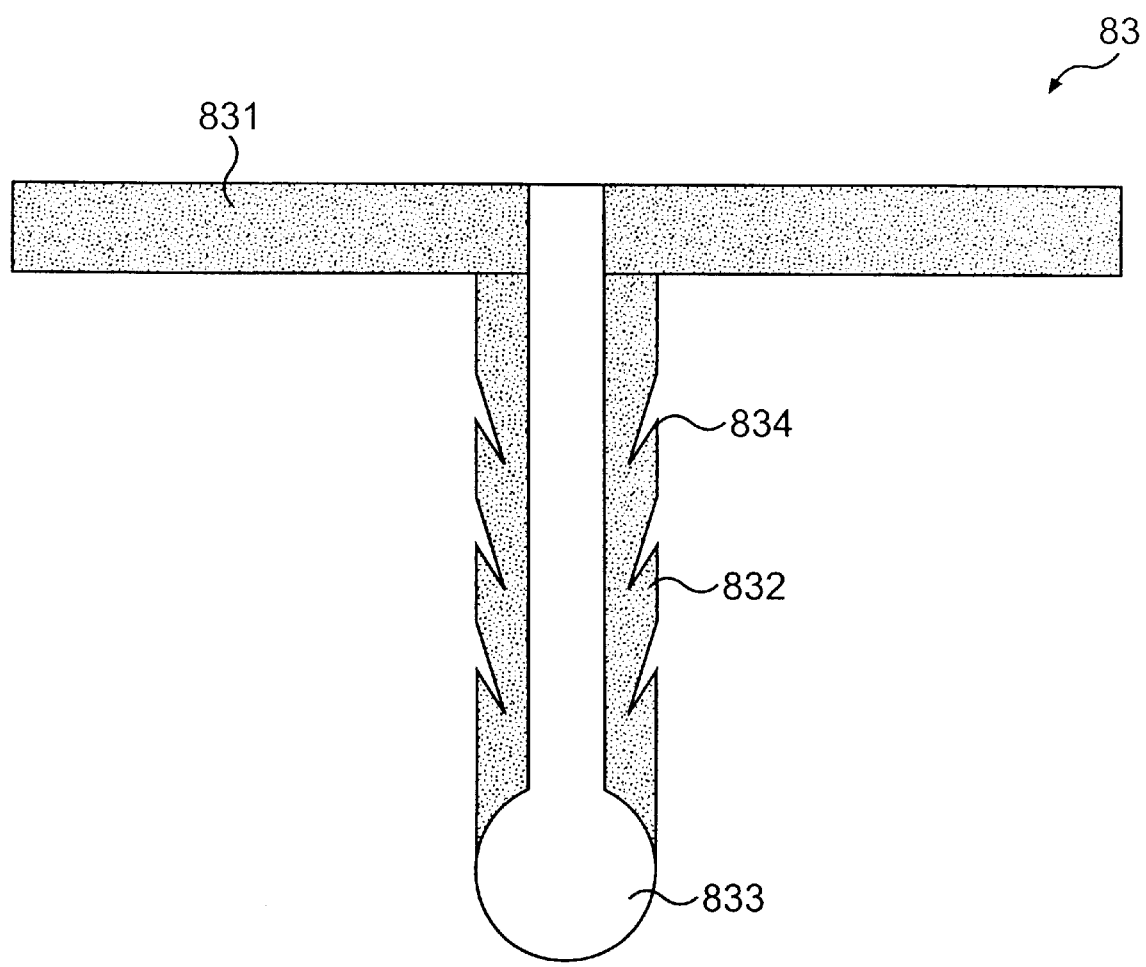
FIG. 72 is a schematic view of a fastener according to another embodiment of the present invention.

FIG. 72 illustrates another embodiment of the endostaple fastener according to the present invention. The endostaple fastener 82 includes a base portion 831 and a spear portion 832. The spear portion 832 includes a heating portion 833 extending there through which permits the insertion of the fastener 83 into the first component 20 and at least a portion of the second component. As described above, the heating portion 833, when heated, burns an opening though the first component and at least a portion of the second component to secure the fastener in place. The spear portion 832 includes at least one hooking assembly 834 which engage the component 20 and vessel 1 to secure the same together. It is contemplated that the base portion 831 may have any one of a variety of shapes. The base portion 831 may be a plate having a circular cross section. Other cross sections including but not limited to rectangular and trapezoidal are considered to be well within the scope of the present invention.

It, however, will be apparent to those skilled in the art that various modifications and variations can be made in the construction and configuration of the present invention without departing from the scope or spirit of the invention. For example, the fastening means mentioned above, may be pop-rivet fasteners, screw-type fasteners, and rapid hardening plastic extrudates, which are all contemplated to be within the scope of the present invention. Thus, it is intended that the present invention cover the modifications and variations of the invention, provided they fall within the scope of the appended claims and their equivalents.

Introducer Sheath Devices

Figures 47, 48:
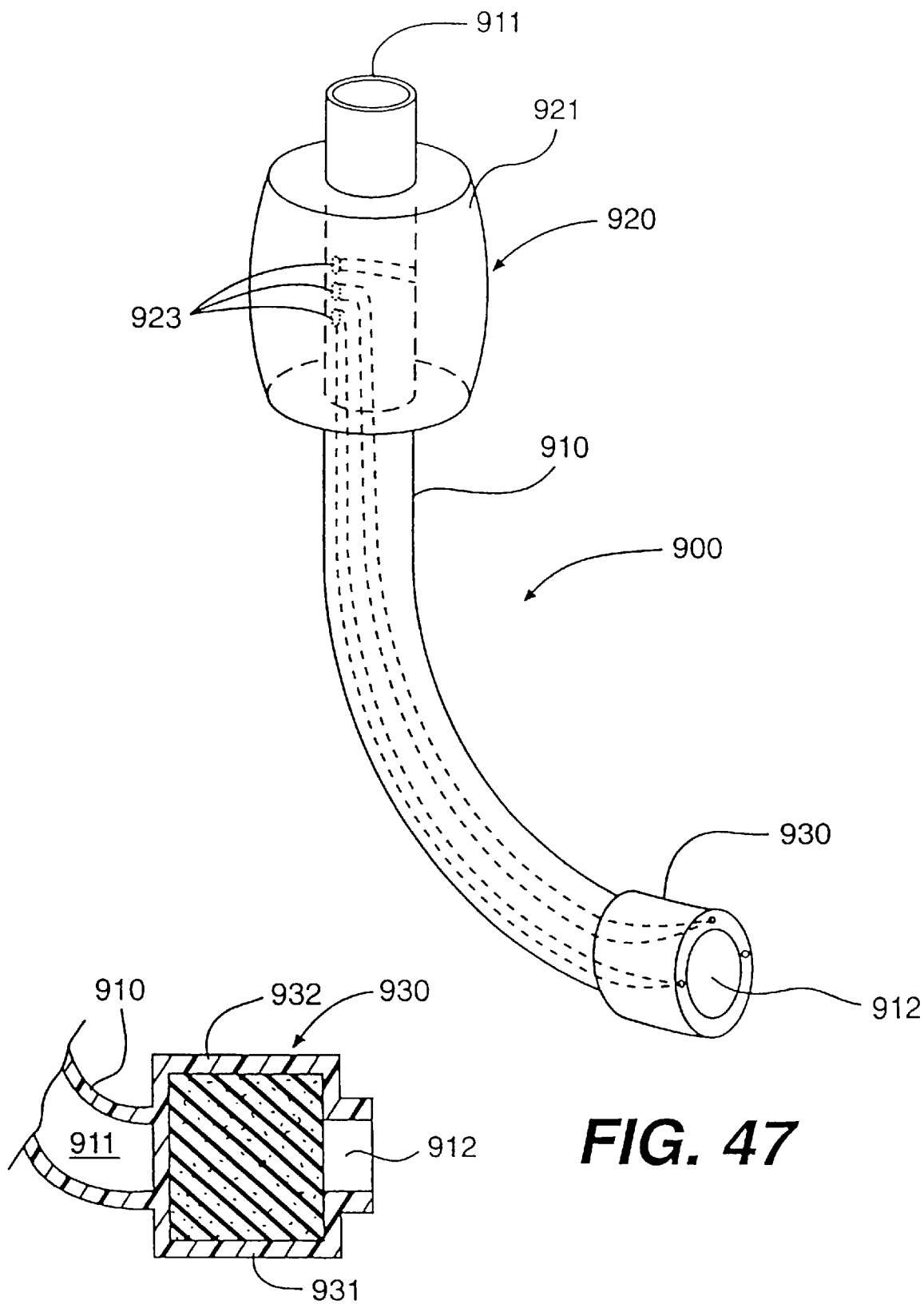
FIG. 47 is a perspective view on an introducer sheath device according to the present invention.
FIG. 48 is a cross sectional view of a seal assembly for the introducer sheath device according to an embodiment of the present invention.

Reference will now be made to a preferred embodiment of an introducer sheath device according to the present invention for use in the repair of abdominal aneurysms, an example of which is illustrated in FIGS. 47 and 48. The introducer sheath device creates a protective passageway through the vessel through which the graft and repair devices are inserted. The introducer sheath device protects the arteries from damage that may occur when the repair apparatus and other devices are passed through the tortuous artery passageways during a surgical procedure.

Existing methods for repairing aneurysms utilize introducer sheath devices only in the femoral and common iliac arteries. Typically, guide wires extend from a femoral arteriotomy to an occlusion balloon placed within the proximal neck of the aorta at a point cephalad with respect to the abdominal aorta. Typically, others have gained access to the abdominal aorta via a femoral or common iliac arteriotomy into which is inserted an introducer sheath device of between 18–28 Fr. diameter. The size of these devices may cause damage to the vessels through which they pass.

By contrast, the inventors of the present invention contemplate the use of more than one unique introducer sheath device 900, as shown in FIG. 47. The sheaths 900 are introduced over a femoral/axillary guide wire. One introducer sheath device 900 extends from either an axillary incision or a brachial incision to the proximal neck of the vessel 1. Another introducer sheath device 900 extends from a femoral incision to the distal neck of the vessel or common iliac/distal aorta transition. The introducer sheath devices according to the present invention that extend through the axillary vessel and through the femoral artery have similar constructions. However, the introducer sheath device that extends through the axillary artery has a smaller size in the range between 9–12 Fr. and is able to navigate the arteriotomy/proximal aorta passageway without problem. The smaller size permits access to the aorta via either the left brachial or axillary artery, both of which are significantly smaller than the femoral or common iliac arteries. This procedure, previously, beyond consideration, may now significantly benefit these vascular procedures.

Each introducer sheath device 900 comprises a housing 910 having a hollow interior 911 that permits the passage of the tube graft and other repair apparatus through the introducer sheath device to the vessel 1. The housing 910 preferably includes multiple lumen or passageways formed therein. The repair apparatus are introduced through a multiport introducer assembly an opening 912 in the end portion of the housing 910. In a preferred embodiment, the housing 910 is a thin walled co-extrusion having an outer surface formed, for example, from silicon and an inner surface formed, for example, from Teflon®. Alternatively, the housing 910 may be formed of a suitable polymer having similar properties.

The introducer sheath device 900, also, comprises positioning assembly 920 for maintaining the sheath 900 in proper orientation within the vessel. In a preferred embodiment, the positioning assembly 920 comprises an inflatable cuff 921 located at one end of housing 910. The positioning assembly 920 further comprises an inflation device for inflating the cuff 921. The inflation device in a preferred embodiment comprises a plurality of passageways 923 formed within the wall of housing 910. A suitable fluid, such as saline, is supplied from an external source through the passageways 923 to fill the cuff 921. The passageways 923 terminate at inflatable cuff 921, as shown in FIG. 47. The positioning assembly 920 includes a silicon balloon which is connected to the housing opposite the introducer assembly. The silicon balloon is preferred for several reasons. First, unlike other polymeric balloons, the silicon balloon is capable of material expansion of up to 800% and will upon deflation return to its original shape. Other materials require "pre-forming" before integration within a device; such a device is more bulky and less able to totally deflate once it has served its clinical purpose. Utilization of silicon facilitates a low profile balloon which can be made co-planar with the multi-lumen housing to which it is attached. Additionally, housing termination details and smooth transitions—balloon to housing, may be affected.

The housing 910 includes a central channel. The housing is formed of a multi-layer assembly comprising a fluorinated polymer core over which a polyurethane layer is extruded. A multi-stranded wire braid is located on top of the polyurethane layer about which a multi-lumen polymeric profile is co-extruded. This housing configuration provides certain benefits. First, the internal surface of the housing also has a low coefficient of friction which aids in the intraluminal passage of both penetration and visualization devices. The braided layer provides kink resistance, torquability and flexibility to the housing, locating the braid within the multi-lumen co-extrusion allows non-destructive access to the peripheral lumen. Furthermore, the co-extruded assembly provides a thermoplastic exterior surface to which the positioning assembly may be readily attached.

Alternatively, the housing may include a multi-lumen polymeric profile about which a multi-stranded wire braid is attached. Thereafter the assembly receives a polymeric coating which binds the three tubular layers to one another.

Prior introducer sheath devices have not been able to control the loss of significant amounts of blood through the open end of the introducer sheath device that is positioned outside of the body. Others have attempted to prevent this blood loss through the use of complex clamping systems. The present invention provides a unique seal arrangement to prevent significant blood loss. The introducer sheath device 900 efficiently seals the smaller surgical devices of the present invention which are typically 3 mm in diameter. Presently available surgical devices used with similar procedures typically have diameters in the range of 6–9 mm. The use of these larger diameter devices in combination with currently available introducer sheaths typically results in significant and problematic blood loss. The sheath 900 may be used with these larger diameter devices without significant blood loss due to its innovative sealing arrangement.

A seal 930 located at one end of the housing 910 adjacent opening 912 prevents significant blood loss. The seal 930 comprises an expanded housing assembly 931. A self-sealing gel-like material 932 is located within the expanded housing assembly 931. The material 932 permits the insertion of the repair apparatus through the material 932, which forms a seal around the repair apparatus. As the repair apparatus is removed from the introducer sheath device 900 and the sealing material 932, the material 932 forms a seal behind the repair apparatus as it is removed through opening 912.

Figure 54:
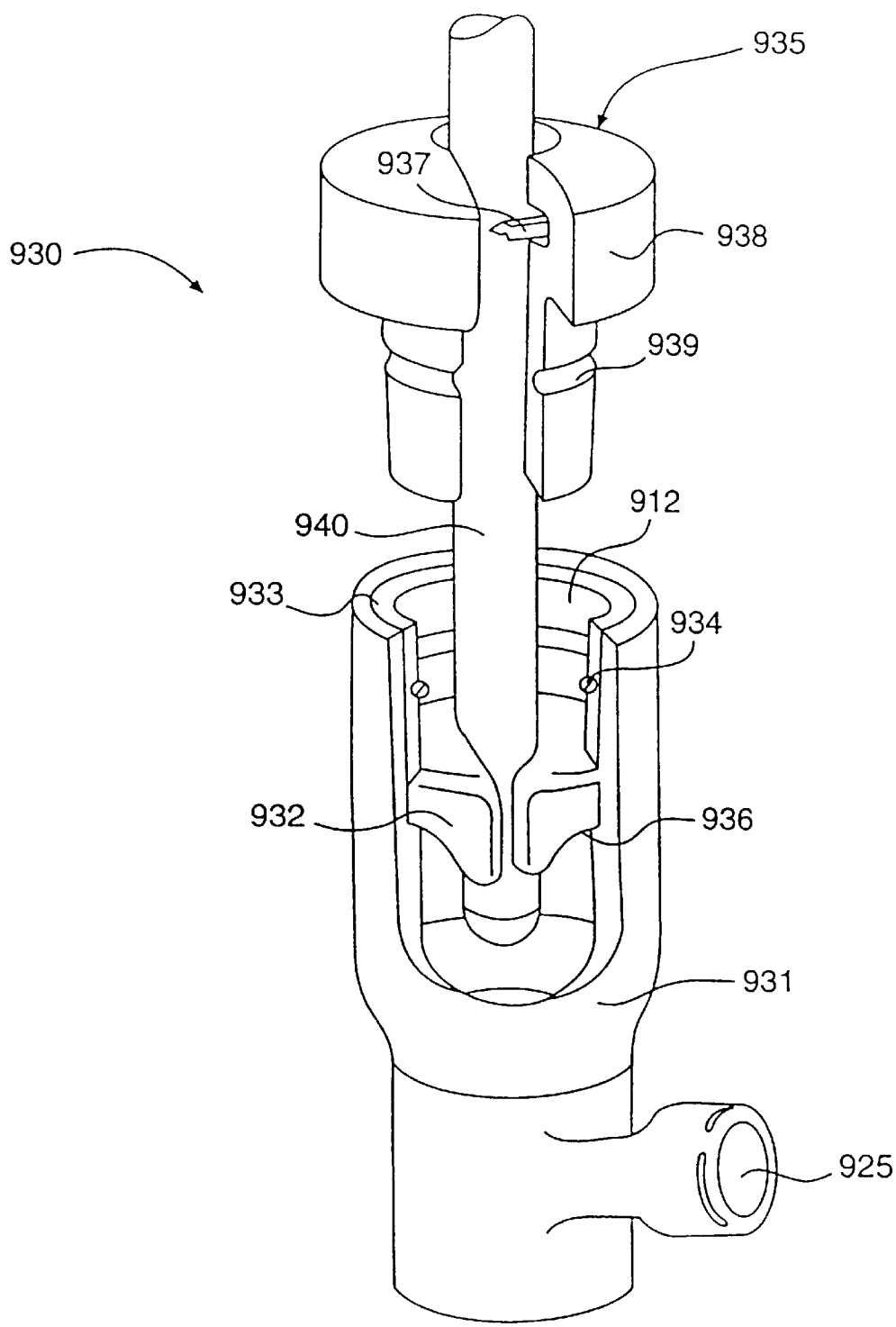
FIG. 54 is a cross sectional view of a seal assembly for the introducer sheath device according to an embodiment of the present invention.

A detailed view of the seal 930 is shown in FIG. 54. The seal assembly 930 may comprise the expanded housing assembly 931 and an end cap 935. The seal material 932 is preferably a polymeric gel, sphincter-like in shape, having a central opening for receiving a surgical device 940. When the surgical device or repair apparatus 940 is removed from the sheath 900 the sphincter-like opening in material 932 closes, creating a tight seal and preventing the loss of blood. The seal material 932 rests on a ledge or seat 936 located in the housing assembly 931. The seal material 932 is held in place by a retaining ring 933, which is secured to the interior of the housing assembly 931.

Figure 55:
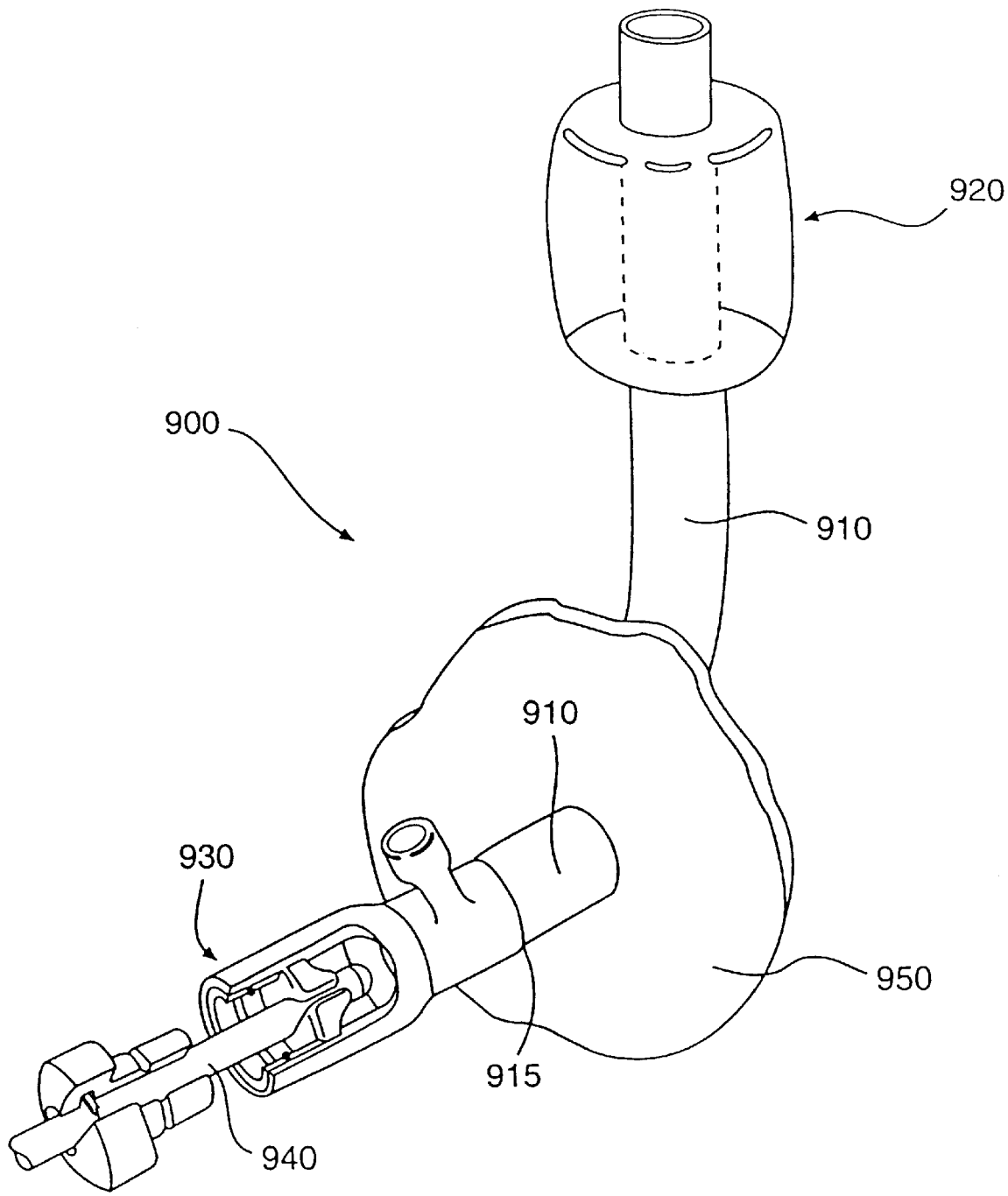
FIG. 55 is a perspective view of the introducer sheath device and seal assembly for the present invention.

The expanded housing assembly 931 is permanently attached to the housing 910, as shown in FIG. 55, at 915. An infusion port 925 is provided to allow for the supply or removal of the fluid or gas, which inflates or deflates the cuff 921. The fluid or gas travels from the infusion port 925 to the cuff 921 via the lumen 923 shown in FIG. 47.

The seal 930 may be used with or without the end cap 935. The end cap 935 provides additional protection against blood loss. The end cap 935 is inserted into the opening 912 in the expanded housing assembly 931 opposite the housing 910. The end cap includes a thumbwheel portion 938 to facilitate connection with the housing assembly 931. The end cap 935 has both internal and external sealing means. The internal sealing means is comprised of a V-type sealing ring 937 which provides a fluid-tight seal between the surgical device 940 and the end cap 935. The external sealing means is provided by an external groove 939 and a sealing ring 934. Sealing ring 934 is preferably an O-ring formed from polymeric material. The end cap 935 may be modified as required to accommodate different surgical devices. The expanded housing assembly 931, however, is capable of accommodating a variety of devices without modification.

The multi-port introducer assembly includes lured entryways for balloon inflation (positioning assembly), pressure monitoring/fluid control. (IVA) and a seat-protected device entry. With the exception of seal and cap details, the multi-port introducer assembly is an insert molding about the housing. The seal includes a thermoplastic elastomer molding having a lubricious polymeric coating, which is able to form a blood-tight seal about inserted instruments having very small diameters while at the same time enabling their easy rotation within the introducer assembly. The cap component snap-fits to the introducer molding and holds the seal component in position.

The general arrangement of the sheath device 900 is shown in FIG. 55. The surgical device or repair apparatus 940 is inserted into the housing 910 through the seal 930 which is located outside the skin 950. As described above, the positioning assembly 920 is located in the vicinity of the aneurysm so maintaining the sheaths 900 correct orientation within the vessel.

It will be apparent to those skilled in the art that various modifications and variations can be made in the construction and configuration ofthe present invention without departing from the scope or spirit of the invention. It is intended that the present invention cover the modifications and variations of the invention, provided they fall within the scope of the appended claims and their equivalents.

While this invention has been described in conjunction with specific embodiments thereof, it is evident that many alternatives, modifications and variations will be apparent to those skilled in the art. Accordingly, the preferred embodiments of the invention as set forth herein are intended to be illustrative, not limiting. Various changes may be made without departing from the spirit and scope of the invention as defined in the following claims.

We claim:

1. A fastener assembly for use in a surgical procedure for securing a first component to a second component, said fastener assembly comprising:

securing means for securing the first component to the second component; and insertion means for inserting said securing means through the first component and at least a portion of the second component, wherein said insertion means comprises incision creating means for creating an incision in the first component and at least a portion of the second component through the application of thermal energy, wherein said securing means and said insertion means have a unitary construction.

2. The fastener assembly according to claim 1, wherein said incision creating means applies heat to create the incision.

3. The fastener assembly according to claim 1, wherein said incision creating means creates the incision by burning the first component and at least a portion of the second component.

4. The fastener assembly according to claim 1, wherein said securing means comprises means of preventing removal of said fastener assembly from the first component and the second component.

5. The fastener assembly according to claim 4, wherein said means for preventing removal includes at least one projection on said fastener assembly extending from said securing means.

6. The fastener assembly according to claim 4, wherein said means for preventing removal includes at least one aperture in said securing means.

7. The fastener assembly according to claim 6, wherein said at least one aperture promotes tissue ingrowth.

8. The fastener assembly according to claim 6, wherein said at least one aperture includes a self-expanding material located therein, wherein said self-expanding material expands upon insertion of said fastener assembly within the first component and the second component.

9. The fastener assembly according to claim 8, wherein said self-expanding material promotes tissue ingrowth.

10. The fastener assembly according to claim 4, wherein said incision creating means applies heat to create the incision.

11. The fastener assembly according to claim 4, wherein said incision creating means creates the incision by burning the first component and at least a portion of the second component.

12. A method of securing a first component to a second component, said method comprising the steps of:

providing a fastener assembly having an incision creating assembly formed therein for creating an incision in the first component and at least a portion of the second component;

positioning said fastener assembly adjacent to the first component at a desired location;

applying electrical energy to said fastener assembly to selectively heat a portion of said fastener assembly such that a portion of the first component and at least a portion of the second component are heated; and applying a force on said fastener assembly to insert said fastener assembly through the portion of the first component and at least a portion of the second component.

13. The method according to claim 12, wherein said step of applying a force on said fastener assembly includes the step of providing an insertion assembly for applying the force to said fastener assembly.

14. The method according to claim 13, wherein the insertion assembly applies the energy to said fastener assembly.

* * * * *